(12) United States Patent
Biddle

(10) Patent No.: US 8,590,367 B2
(45) Date of Patent: Nov. 26, 2013

(54) PORTABLE BRINELL HARDNESS TESTER

(75) Inventor: Ernest L. Biddle, Bryn Mawr, PA (US)

(73) Assignee: King Tester Corporation, King of Prussia, PA (US)

( * ) Notice: Subject to any disclaimer, the term of this patent is extended or adjusted under 35 U.S.C. 154(b) by 0 days.

(21) Appl. No.: 13/222,290

(22) Filed: Aug. 31, 2011

(65) Prior Publication Data

US 2013/0047698 A1 Feb. 28, 2013

(51) Int. Cl.
*G01N 3/48* (2006.01)
*F16K 17/00* (2006.01)

(52) U.S. Cl.
USPC .............................. 73/81; 137/539.5

(58) Field of Classification Search
USPC ................ 73/1.01, 81; 137/539.5, 540
See application file for complete search history.

(56) References Cited

U.S. PATENT DOCUMENTS

| | | |
|---|---|---|
| D31,361 S | 8/1899 | Ball |
| D34,213 S | 3/1901 | Baxter |
| 827,846 A | 8/1906 | Bowser et al. |
| 1,209,350 A | 12/1916 | Steiner |
| 1,232,782 A | 7/1917 | Field |
| 1,354,218 A | 9/1920 | Schneider |
| 1,384,389 A | 7/1921 | Johnson |
| 1,431,832 A | 10/1922 | Mills et al. |
| 1,646,195 A | 10/1927 | German |
| D78,990 S | 7/1929 | Stevenson |
| 1,770,045 A | 7/1930 | Shore et al. |
| 1,973,333 A | 9/1934 | Craemer |
| 2,029,066 A | 1/1936 | Geppert |
| 2,203,129 A | 6/1940 | Campbell et al. |
| 2,297,778 A | 10/1942 | Knerr et al. |
| 2,319,208 A | 5/1943 | Clark |
| 2,337,573 A | 12/1943 | Schultz |
| 2,391,394 A | 12/1945 | Cogbill |
| 2,418,916 A | 4/1947 | Weaver |
| 2,448,486 A | 8/1948 | Chester |
| 2,466,567 A | 4/1949 | Williams |
| 2,532,027 A | 11/1950 | Maddox |
| 2,535,830 A | 12/1950 | Beck |
| D168,385 S | 12/1952 | Watson |
| 2,643,544 A | 6/1953 | Chester |
| 2,693,698 A | 11/1954 | Scott |
| D178,060 S | 6/1956 | Karol |
| 2,804,769 A | 9/1957 | Clark, Sr. |
| 2,835,127 A | 5/1958 | Scott |

(Continued)

FOREIGN PATENT DOCUMENTS

| | | |
|---|---|---|
| DE | 2357755 | 6/1974 |
| DE | 2751095 | 3/1979 |

OTHER PUBLICATIONS

International Search Report for PCT/US2012/052979, dated Dec. 26, 2012.
Written Opinion for PCT/US2012/052979, dated Dec. 26, 2012.

*Primary Examiner* — Hezron E Williams
*Assistant Examiner* — David Z Huang
(74) *Attorney, Agent, or Firm* — Charles N. Quinn; Fox Rothschild LLP

(57) ABSTRACT

A portable Brinell metal hardness tester has a test head mounted in a carriage, movable vertically along elevating screws, and includes an adjustable valve for relieving hydraulic pressure within the test head where the valve includes a stem, an interior member, and an intermediate member.

12 Claims, 13 Drawing Sheets

(56) References Cited

U.S. PATENT DOCUMENTS

| | | | |
|---|---|---|---|
| 2,839,917 A | 6/1958 | Webster | |
| 2,956,432 A | 10/1960 | Henrikson | |
| 2,966,083 A | 12/1960 | North | |
| 2,976,723 A | 3/1961 | Eddy | |
| 3,029,631 A | 4/1962 | Borgerson et al. | |
| 3,083,598 A | 4/1963 | Kinnison | |
| 3,102,417 A | 9/1963 | Chambers | |
| 3,128,621 A | 4/1964 | Scott | |
| 3,129,582 A * | 4/1964 | Borgersen | 73/81 |
| 3,138,951 A | 6/1964 | Scott | |
| 3,156,143 A | 11/1964 | Wolf | |
| D200,799 S | 4/1965 | Dickman | |
| D203,933 S | 3/1966 | Griffith | |
| 3,247,824 A | 4/1966 | Rodgers | |
| 3,309,916 A | 3/1967 | Pearson | |
| 3,370,421 A | 2/1968 | Piper | |
| 3,478,568 A | 11/1969 | Borgerson | |
| 3,486,373 A | 12/1969 | Scott | |
| D219,861 S | 2/1971 | Coffman | |
| D223,174 S | 3/1972 | Pettavel | |
| 3,728,551 A | 4/1973 | Culver et al. | |
| 3,754,436 A * | 8/1973 | Saxton | 73/81 |
| 3,815,125 A | 6/1974 | May et al. | |
| 3,908,489 A | 9/1975 | Yamamoto et al. | |
| 3,980,066 A | 9/1976 | Hollins | |
| 4,036,048 A | 7/1977 | Webster | |
| 4,075,478 A | 2/1978 | Walker | |
| 4,094,188 A | 6/1978 | Bellouin et al. | |
| 4,147,052 A | 4/1979 | Tsujiuchi et al. | |
| 4,193,199 A | 3/1980 | Whiteley et al. | |
| 4,312,220 A | 1/1982 | Borgersen et al. | |
| 4,361,034 A * | 11/1982 | Borgersen et al. | 73/81 |
| 4,562,758 A | 1/1986 | Stirling | |
| D283,599 S | 4/1986 | Biddle et al. | |
| 5,388,486 A | 2/1995 | Ruzicka et al. | |
| D369,968 S | 5/1996 | Decursu et al. | |
| D387,640 S | 12/1997 | Von Fange | |
| D406,993 S | 3/1999 | Jones | |
| 6,050,165 A | 4/2000 | Hall | |
| 6,516,689 B1 | 2/2003 | Bates | |
| 6,837,266 B2 * | 1/2005 | Fredrickson et al. | 137/529 |
| 6,908,113 B2 | 6/2005 | Chaduc et al. | |
| 7,000,505 B2 * | 2/2006 | Hsien | 81/121.1 |
| 2006/0214789 A1 * | 9/2006 | Posamentier et al. | 340/545.6 |
| 2008/0041470 A1 * | 2/2008 | Golan et al. | 137/625.41 |
| 2008/0078460 A1 * | 4/2008 | Roper et al. | 137/540 |
| 2008/0083460 A1 * | 4/2008 | Yang | 137/315.15 |

* cited by examiner

PORTABLE BRINELL HARDNESS TESTER

BACKGROUND OF THE INVENTION

1. Field of the Invention

This invention relates generally to metal hardness testers and specifically to portable metal hardness testers using the Brinell method of hardness testing.

2. Description of the Prior Art

The portable Brinell metal hardness tester disclosed and claimed in U.S. Pat. No. 3,129,582 has, over the past fifty years, become the standard of the world for portable Brinell metal hardness testers. The U.S. Pat. No. 3,129,582 tester has been and is commercially successful and has been copied prolifically since the '582 patent expired. Portable metal hardness testers that are literally bolt-for-bolt copies of the apparatus disclosed and claimed in U.S. Pat. No. 3,129,582 are readily available all over the world. One need only to perform a Google search for "portable Brinell metal hardness tester" to find literally hundreds of sources of supply of machines that are visually indistinguishable from the apparatus disclosed in U.S. Pat. No. 3,129,582.

The same commercial success and third party copying is true respecting the portable Brinell metal hardness tester disclosed and claimed in the U.S. Pat. No. 4,361,034, which is an improvement over the tester disclosed and claimed in U.S. Pat. No. 3,129,582.

While the portable Brinell metal hardness testers disclosed and claimed in U.S. Pat. Nos. 3,129,582 and 4,361,034 have been commercially highly successful, improvements can always be made even in the most successful of products, including the '582 and '034 portable Brinell metal hardness testers.

An occasional annoyance when calibrating the tester or when changing the hydraulic fluid in the portable Brinell metal hardness tester of the type disclosed in U.S. Pat. Nos. 3,129,582 and 4,361,034 is leakage of hydraulic fluid occurring during the calibration or oil change process. The process is messy in that hydraulic fluid, namely oil, inevitably escapes. Moreover, there is always risk of contamination of the hydraulic fluid in the course of the changing of the fluid and/or calibration of the tester.

Another problem arising occasionally is that overzealous technicians, in the course of manually pumping the tester while making a test, inadvertently or perhaps sometimes semi-intentionally pull the pump handle through a greater range of angular travel than for which the tester was designed, thereby either breaking the pump handle or damaging the internal gears of the oil pump within the tester. In either case, the tester is rendered inoperative until it is repaired.

A third problem in using the testers of the '582 and '034 patents is that of technician tampering with the tester once the tester has been calibrated. Neither the '582 tester nor the '034 tester has any means to detect tampering once the tester has been calibrated.

Yet another minor problem with the testers of '582 and '034 patents is that the handle for the pressure release valve is difficult to grasp. Sometimes it may be necessary for the operator to rapidly release the hydraulic pressure within the tester. The handle for the pressure release valve in both the '582 and '034 patent testers is difficult to grasp by an adult, making quick action in opening the pressure release valve difficult.

SUMMARY OF THE INVENTION

This invention provide substantial improvements to portable Brinell metal hardness testers of the type disclosed in the U.S. Pat. Nos. 3,129,582 and 4,361,034 by facilitating rapid manual release of hydraulic pressure when required; prevention of breakage of the hydraulic pump mechanism; easier, faster and cleaner calibration and hydraulic oil change; and detection of tampering with the tester, particularly of the calibration setting for the tester.

This invention facilitates quick adjustment and calibration of portable Brinell metal hardness testers of the type disclosed in U.S. Pat. Nos. 3,129,582 and 4,361,034, without contaminating the hydraulic fluid, typically oil, in the tester. With this invention, the loads involved may be changed quickly without contaminating oil in the tester The invention facilitates faster adjustment of the tester and more precise adjustment of the tester than was previously possible when calibrating by either direct or indirect verification using methodologies disclosed in the American Society for Testing Materials Publication E10 for Brinell tester calibration.

Heretofore, when calibrating or changing oil and recalibrating a portable Brinell metal hardness tester of the type disclosed in U.S. Pat. Nos. 3,129,582 and 4,361,034, one had to perform the following steps: (i) remove the socket head screw over the pop-off pressure relief valve located within an internal bore of the machine test head; (ii) place the test block or load cell on the tester anvil and begin the test procedure; (iii) with a screwdriver, adjust the load by turning a calibrating nut either right or left to adjust the load; and (iv) when finished calibrating, reinstall and tighten the socket head screw and copper gaskets of the pressure relief valve so that oil could not escape. This process was messy and allowed contamination of the hydraulic fluid, namely oil, used in the hydraulic portion of the tester.

In one aspect, the invention provides a pressure relief valve with an external cap that is removable by hand whereupon the tester may be adjusted by turning an extended hex head screw. The pressure relief valve external cap protects the external calibrating hex head screw from damage and prevents leakage of hydraulic fluid to the tester exterior from the pressure release valve.

In another one of its aspects, this invention provides a portable metal hardness tester having a test head for applying preselected force to a test piece by application of preferably manually-pumped hydraulic fluid into a ram pressure chamber to move a ram cylinder within the test head towards the test piece, where the test head includes an externally adjustable pressure relief valve residing within a threaded passageway extending from the test head exterior into contact with the hydraulic fluid.

The pressure relief valve preferably includes a stem having a circular head adapted to fit sealingly against a seat formed in a passageway in the test head, with the passageway communicating with the hydraulic fluid within the test head and connecting to the ram pressure chamber. The pressure relief valve preferably further includes a shaft having a first end integrally formed with and extending coaxially from the circular head. The pressure relief valve preferably yet further includes a spring for biasing the stem against the seat, with the spring residing slidably about the shaft.

The pressure relief valve preferably yet further includes an annular cap slidably receiving a second end of the shaft through a central aperture, with the spring contacting the cap outboard of the central aperture. The pressure relief valve preferably yet further includes an internal member having a first end with a circular recess adapted for receiving the annular cap therewithin, with the first end being externally threaded for engagement with corresponding threads formed in the passageway. The internal member preferably further includes a central shaft portion and a second end having an axially facing receptacle for receiving a hexagonal wrench therewithin for manual rotation of the intermediate member.

The pressure relief valve preferably yet further includes the aforementioned external cap having a cylindrical bore therein with the bore being adapted to slidably receive the internal member via an opening thereto and with the remaining end of the bore being closed, with the bore being of sufficient depth to receive the internal member when the cap is in facing engagement with the test head.

The pressure relief valve yet further includes an axially elongated intermediate member having a central preferably cylindrical passageway extending therethrough. The axially elongated intermediate member includes a central portion preferably having a hexagonal exterior with an annular shoulder preferably being formed about the passageway on one end of the central portion and having an axially facing annular surface preferably formed on the opposite end of the central portion. The intermediate portion further includes a first larger end portion of generally tubular configuration extending preferably coaxially with the central cylindrical bore and being externally threaded for mating engagement with the threaded passageway. The axially elongated intermediate member still further preferably includes a smaller second end portion of generally tubular configuration, extending coaxially with the central cylindrical bore and being externally threaded at the end thereof remote from the central portion. The external threads of the smaller second end portion of the intermediate member mesh with internal threads in a bore in the external cap, which is removable.

The pressure relief valve of the invention is retrofitable to portable Brinell hardness testers of a type disclosed in the U.S. Pat. Nos. 3,192,582 and 4,361,034 as manufactured by King Tester Corporation, King of Prussia, Pa., and in bolt-for-bolt copies of these testers as made by numerous copyists around the world.

When assembled, the valve has the recess of the interior member cylindrical first end fitting over and receiving the lesser diameter second portion of the cylindrically configured cap, with the bore of the interior member cylindrical first end portion preferably positioned to receive the shaft upon axial movement of the circular head and resultant compression of the spring. The external threads on the interior member first end are of the same diameter and pitch as those on the externally threaded surface of the larger first end of the intermediate member, with both sets of external threads being adapted to threadedly engage a passageway in which the valve is to be positioned.

The pressure relief valve preferably further has an axially facing annular surface of the cylindrical first end of the interior member and an axially facing annular surface of the intermediate member first end that are in facing contact with one another. The elongated central cylindrical portion of the interior member extends slidably through the central cylindrical passageway of the intermediate member. The cylindrical second end of the interior member preferably extends slidably through and outwardly of the intermediate member, preferably providing access to the horizontal receptacle of the interior member first end. With this arrangement, upon manual hexagonal wrench rotation of the interior member, the interior member preferably moves axially within the threaded passageway due to threaded engagement thereof with the threaded passageway. The interior member cylindrical first end preferably moves the cap axially, with the valve stem exerting greater or lesser force at the valve seat according to the direction of axial movement of the interior member, thereby compressing or relieving the spring.

In yet another one of its aspects, this invention provides a portable metal hardness tester with a test head preferably mounted in a carriage for applying preferably preselected force to a test piece. The force is preferably generated by application of manually-pumped hydraulic fluid into a ram pressure chamber preferably to move a ram cylinder within the test head towards the test piece, where the portable metal hardness tester preferably includes a pumping handle mounted on a rotatable shaft connected to the test head, and gears within the test head for converting rotary motion of the shaft, resulting from operator applied manual force to the pumping handle, into longitudinal movement of a hydraulic fluid pumping piston within the test head, with a stop preferably being connected to the carriage for limiting angular movement of the pumping handle turning the rotatable shaft.

The "stop" or stroke limiter structure of the portable Brinell metal hardness tester embodying the invention prevents breakage of the tester hydraulic pump gear and rack combination, which may otherwise result from overzealous use of the tester when overeager or undereducated operators inadvertently apply excessive of force to the pump handle. The stop or stroke limiter structure limits the length of the stroke of the pump handle, at the end of the stroke, in such a way as to prevent the pump handle from being overextended and perhaps breaking. The stroke limiter structure does not interfere with operation of the portable Brinell metal hardness tester. However, presence of the stop or stroke limiter structure may require the operator to make two or three additional strokes of the pump handle in order to reach and apply the maximum load of 3,000 kg. of force. It does not affect lower loads such as 500 kg., 1,000 kg., and 1,500 kg.

The stroke limiter stop structure portion of the portable Brinell metal hardness tester manifesting aspects of the invention may be removed once the operator learns proper operation of the portable Brinell metal hardness tester. The stroke limiter structure may also be retrofitted to portable Brinell metal hardness testers of the type disclosed in U.S. Pat. Nos. 3,129,582 and 4,361,034.

In yet still another one of its aspects, this invention provides a portable Brinell metal hardness tester including a carriage moveable along vertically elongated elevating screws, a test head mounted in the carriage for applying preselected force to a test piece, where the test head includes a pressure release valve, with the pressure release valve including a shaft extending outwardly from the test head and an upstanding handle for actuation of the pressure release valve. The handle preferably includes a ring-like portion with a preferably internally fluted aperture formed therein for receiving and gripping the extending shaft portion of the pressure release valve.

The pressure release valve handle portion preferably has a planar lower surface for flush fitting with an exterior surface of the test head. The handle further preferably includes a blade-like extension portion configured for gripping between an operator's thumb and forefinger, with the extension portion extending vertically away from the preferably planar lower surface of the handle a distance greater than the ring-like portion. The extension portion preferably further includes a first vertically extending edge extending proximate the ring-like portion and a second vertically extending edge preferably at an extremity remote from the ring-like portion, with the second vertically extending edge preferably being longer than the first vertically extending edge, and with extremities of the first and second vertically extending edges remote from the planar surface preferably being connected by a straight edge.

In yet another one of its aspects, this invention provides a tampering detector for use with a portable Brinell hardness tester having a test head for applying preselected force to a test piece, by manual pumping of hydraulic fluid to apply hydraulic fluid pressure of a preselected level to a ball contacting a test piece, where the test head includes an adjustable pressure relief valve, preferably of the type described above, for relieving hydraulic fluid pressure at an adjustably selected level. The adjustable pressure relief valve has a preferably external cylindrical cap portion at one extremity with the external cylindrical cap having a threaded bore for the connection with an intermediate portion of the pressure relief valve extending from the test head. The cylindrical cap is preferably exterior of the test head.

The tampering detector preferably comprises a laminar sheet preferably having a first portion with a preferably circular periphery for fitting on a circular top of the valve cylindrical cap, a second portion having preferably parallel sides and extending radially away from the first portion, and a third portion connected to the second portion remotely from the first portion, having preferably parallel sides that are preferably perpendicular to the sides of the second portion. Adhesive preferably secures the sheet first portion to the cylindrical cover and the sheet third portion to the valve intermediate portion extending from the test head, so that the sheet must be torn when separating the valve cap from the valve intermediate portion, thereby indicating tampering with the pressure relief valve. In one embodiment, the sheet is preferably paper. In another embodiment, the sheet is preferably polymeric. The sheet desirably accepts ink. Also desirably, the circular periphery of the first portion is of lesser diameter than the cylindrical cover.

In yet another one of its aspects, the invention provides a pressure relief valve as a standalone valve, usable in hydraulic apparatus where pressure relief control is needed, with the valve being as described above in combination with the portable Brinell metal hardness tester.

DESCRIPTION OF THE PREFERRED EMBODIMENTS AND BEST MODE KNOWN FOR PRACTICE OF THE INVENTION

Figure 1:
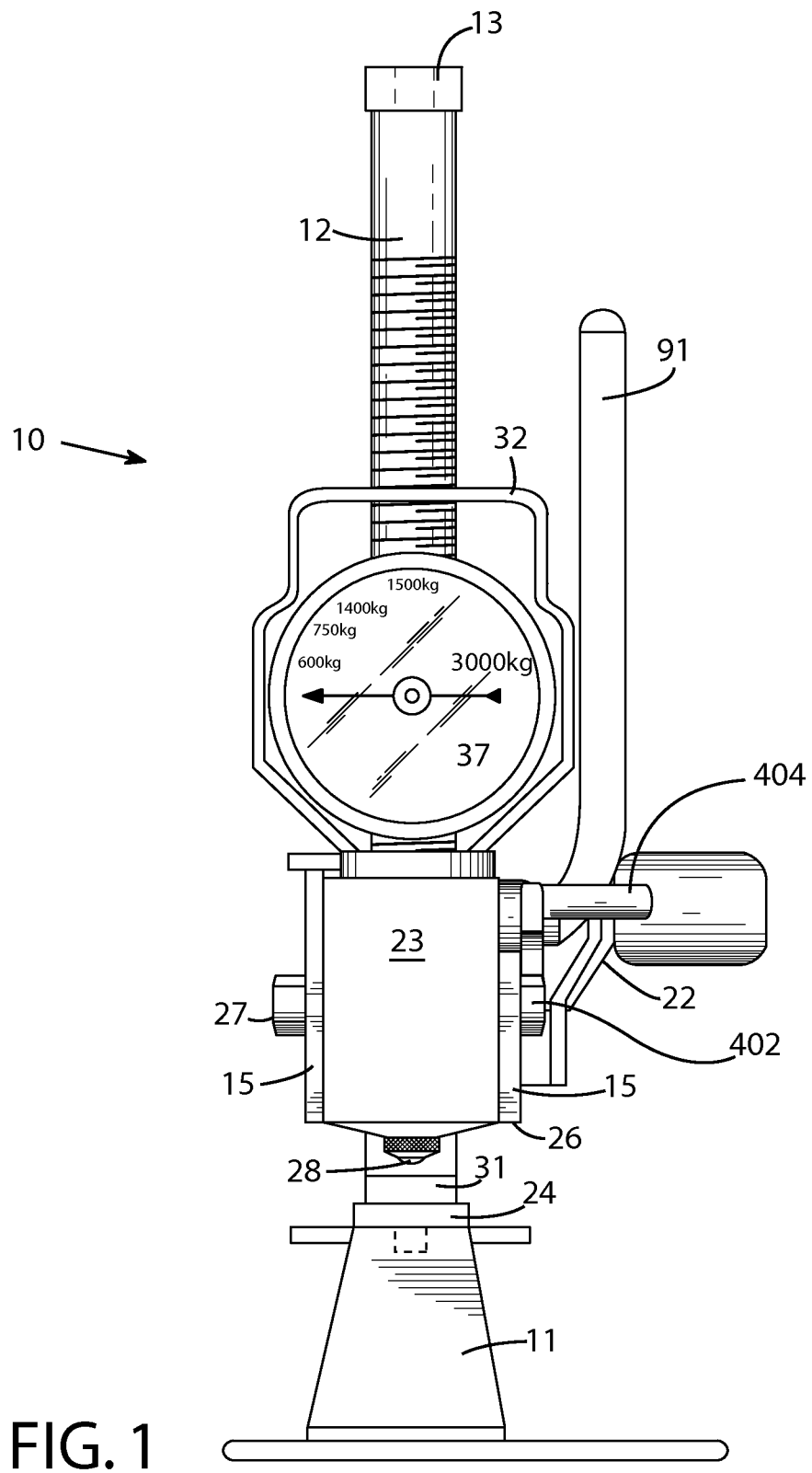
FIG. 1 is a front elevation of a portable Brinell metal hardness tester manifesting aspects of the invention.
Figure 2:
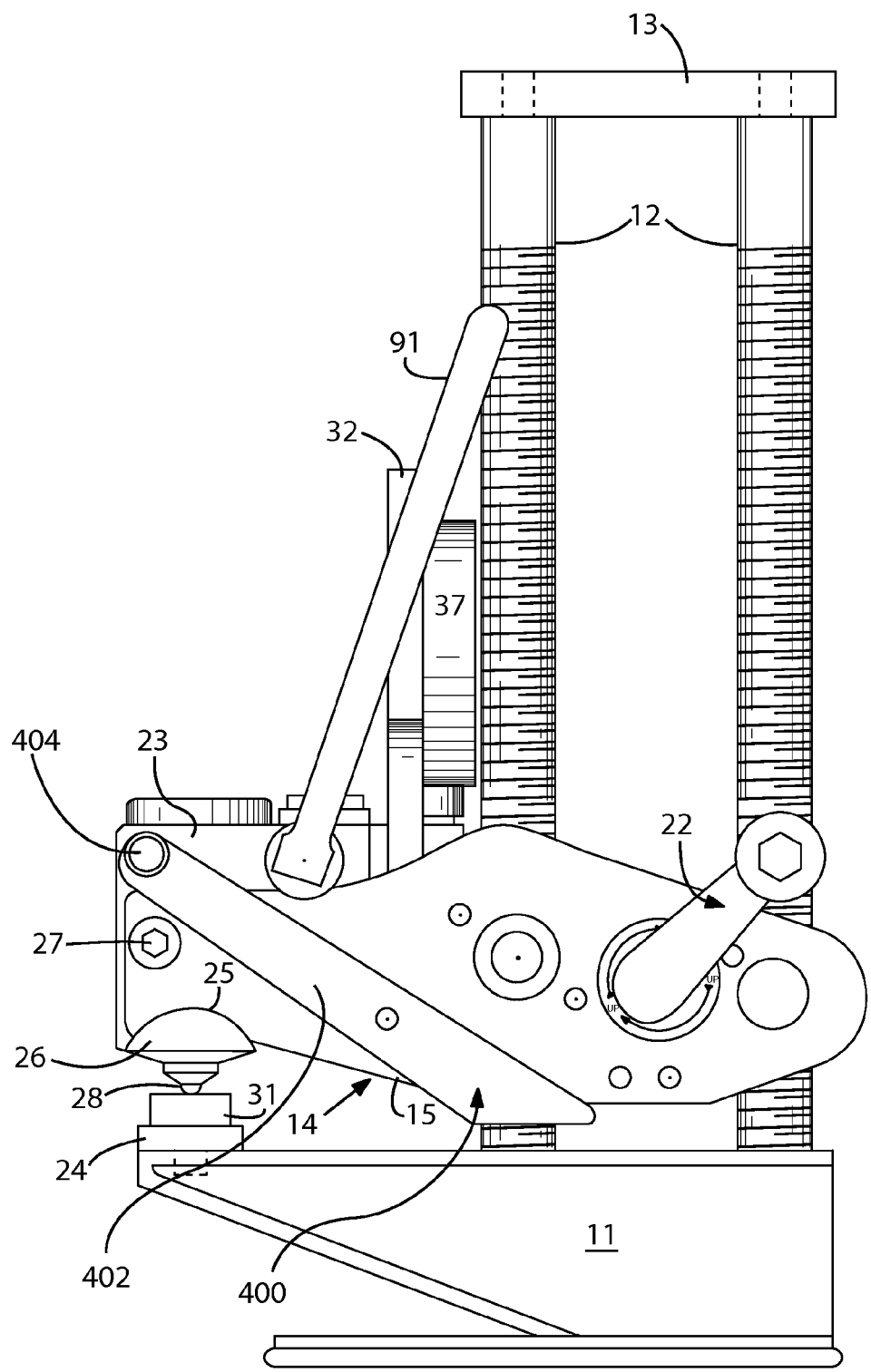
FIG. 2 is a left side elevation of the portable Brinell metal hardness tester illustrated in FIG. 1, with a pumping lever shown spaced from the a pump stroke limiter.

Referring generally to FIGS. 1 through 9 of the drawings, and particularly to FIGS. 1 and 2, a portable Brinell metal hardness tester designated generally 10 includes a base 11 supporting a pair of upstanding elevating screws 12, which are preferably connected together at the top by a horizontal strap 13. Strap 13 helps maintain screws 12 parallel and also provides a handle by which the portable Brinell metal hardness tester may be carried.

A carriage 14 is mounted for preferably vertical movement along the two elevating screws 12. Carriage 14 includes two parallel side plates 15 preferably connected together by blocks 16, shown best in FIG. 4, held in place by suitable bolts, not numbered in the drawings and which rotatably support ring gears 17, the internal teeth of which mesh with elevating screws 12. The external teeth of ring gears 17 are driven by a gear 18, rotating about a vertical axis. Gear 18 meshes with a gear 21, which is driven by a hand crank assembly 22. By manually turning a handle portion of hand crank assembly 22 and thereby rotating the crank 22 of hand crank assembly, ring gears 17 rotate. As the internal teeth of ring gears 17 engage the external threads of elevating screws 12, carriage 14 is raised or lowered as desired.

Figure 4:
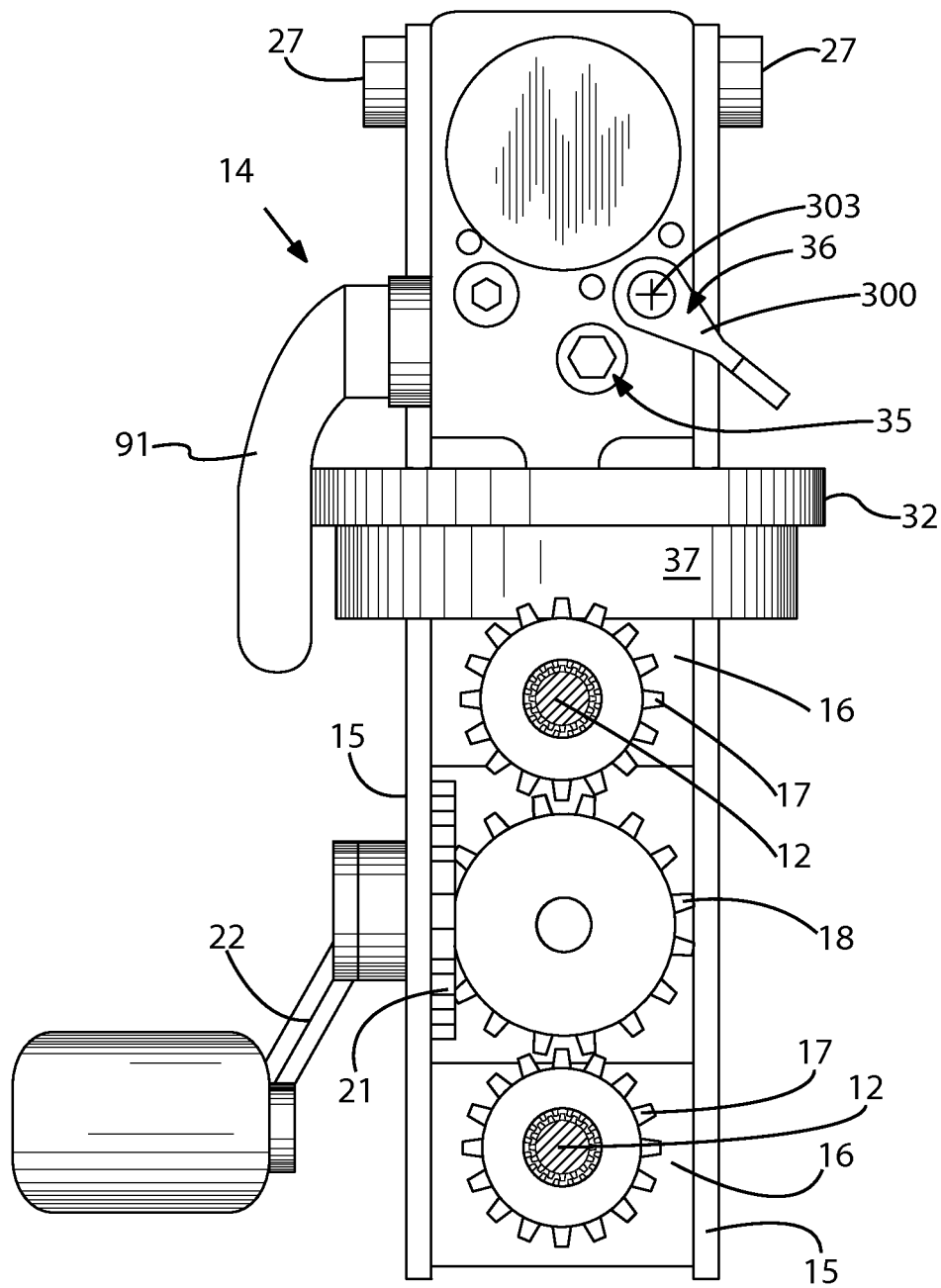
FIG. 4 is a top plan view, in somewhat schematic form, of the portable Brinell metal hardness tester illustrated in FIGS. 1 through 3, with the carrying handle removed and the elevating screws depicted in section.

As best shown in FIGS. 2 and 4, the front ends of side plates 15 are spaced apart and receive a test head 23, which is maintained in a predetermined position thereby over an anvil 24. Anvil 24 is supported on base 11. Downwardly facing arc-shaped surfaces 25 formed in side plates 15 engage correspondingly shaped arc-shaped ears 26 extending from the sides of test head 23, thereby maintaining test head 23 in position respecting anvil 24. Screws 27 hold side plates 15 against test head 23.

As apparent from FIG. 2, arcs defining arc-shaped surfaces 25 and corresponding arc-shaped surfaces of ears 26 are struck from an axis which includes the center of a ball 28, which in turn is carried by test head 23. The axis extends normal to the path of movement of ball 28, whereby forces acting through arc-shaped surfaces 25, when the tester is in use, are substantially radial with respect to ball 28. As a result, lateral thrust due to off-center application of force to ball 28, and consequent inaccurate test readings, are both minimized.

When a test piece, such as that shown as 31, is placed between ball 28 and anvil 24 as illustrated in FIGS. 1 and 2, portable Brinell metal hardness tester 10 may be operated to determine hardness of the test piece 31.

Test head 23 may be removed from carriage 14 by loosening screws 27 and lifting head 23 from between side plates 15 using handle 32.

Figure 5:
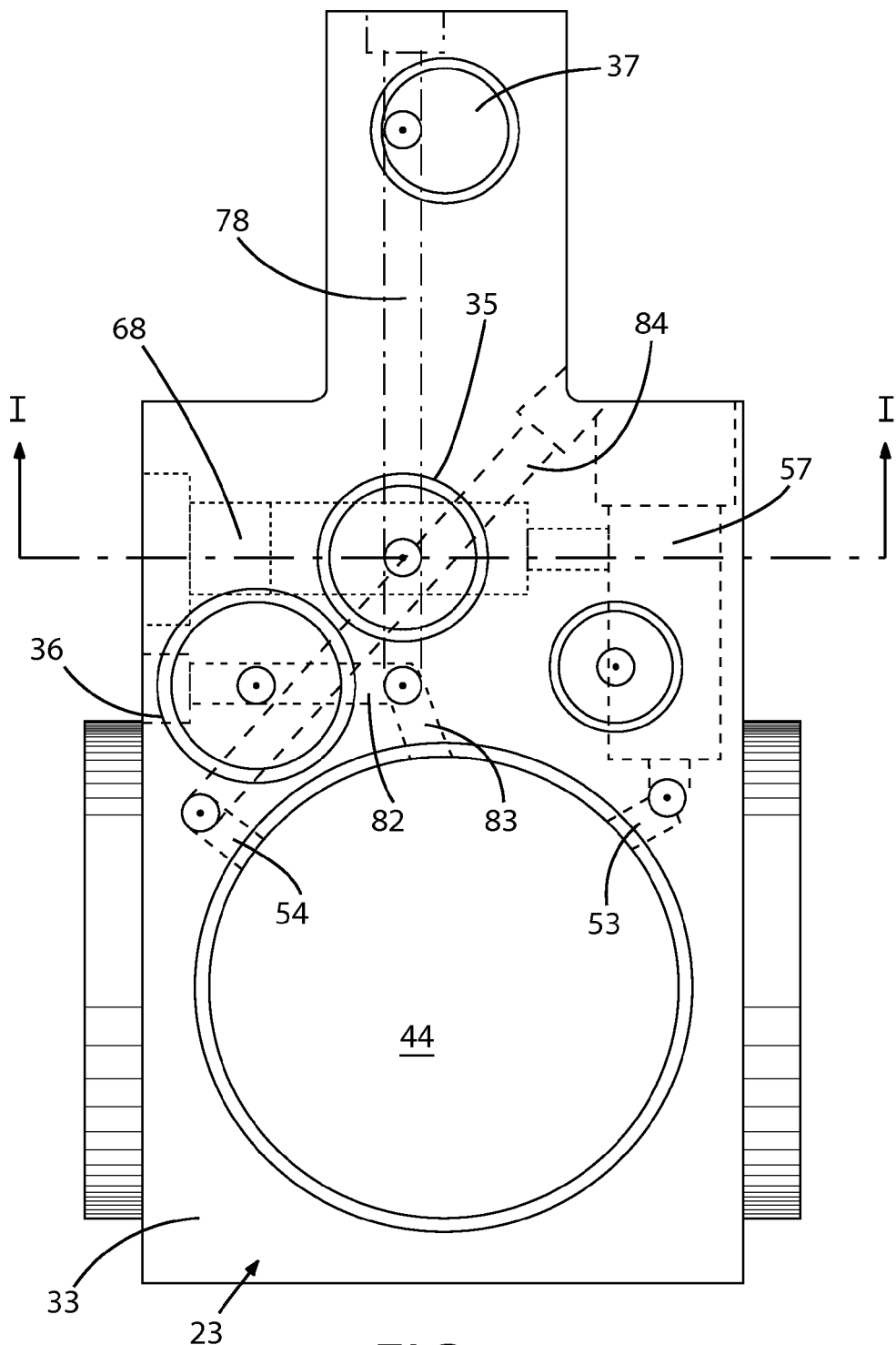
FIG. 5 is a top plan view of a test head portion of the portable Brinell metal hardness tester illustrated in FIGS. 1 through 4.
Figure 6:
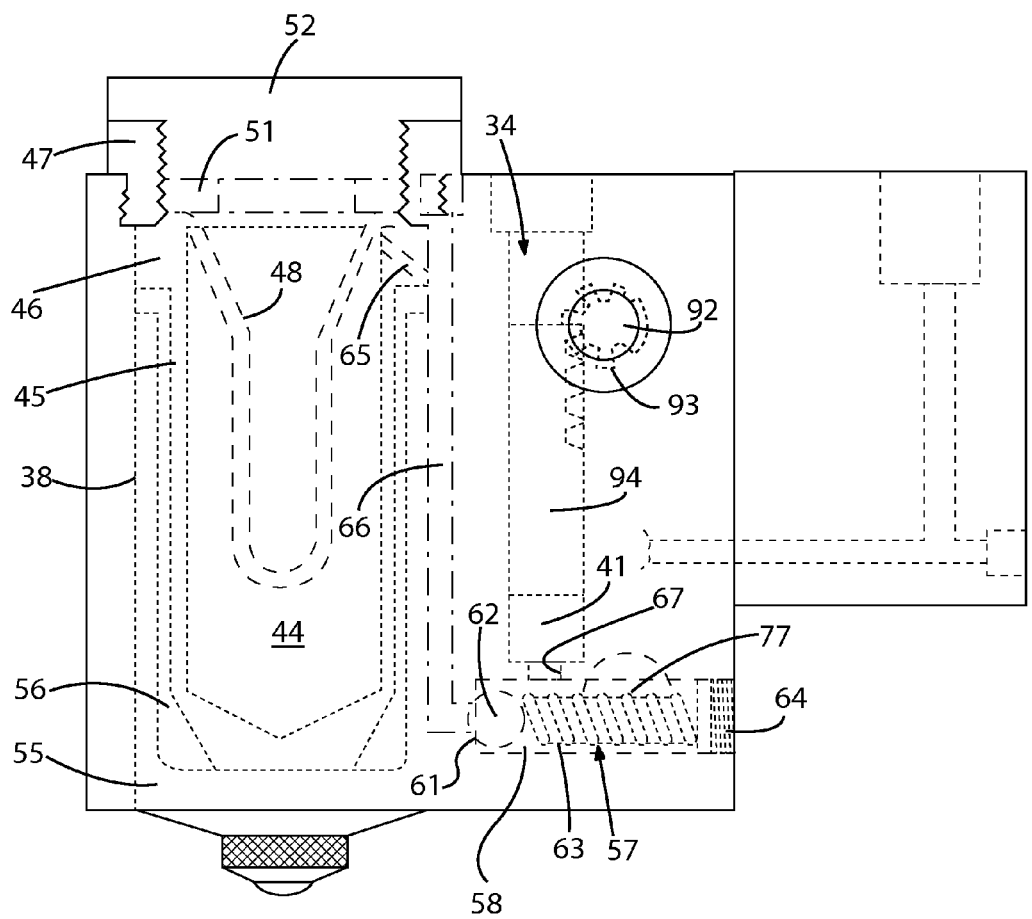
FIG. 6 is a right side elevation of the test head illustrated in FIG. 5.
Figure 7:
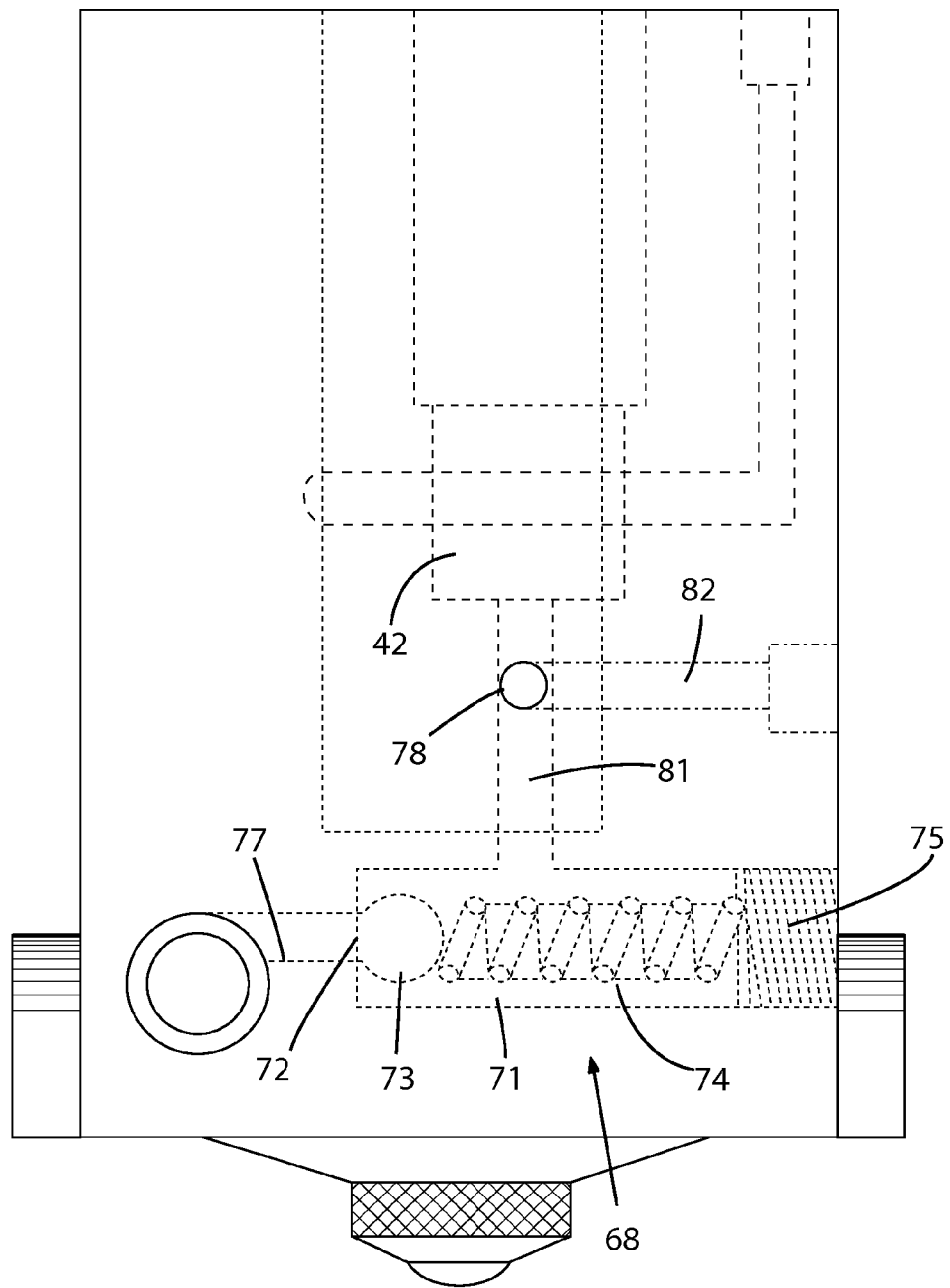
FIG. 7 is a rear elevation of the test head illustrated in FIGS. 5 and 6.
Figure 8:
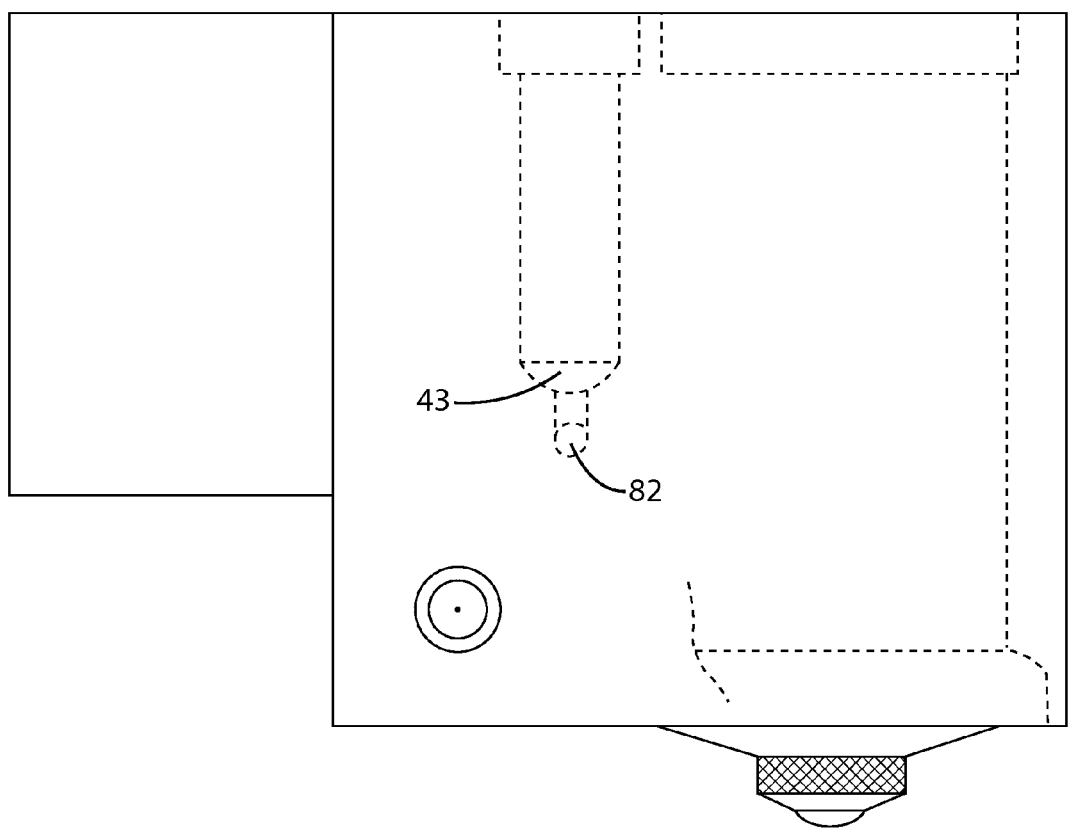
FIG. 8 is a left side elevation of the test illustrated in FIGS. 5, 6 and 7.

Referring principally to FIG. 5, and also to FIGS. 6, 7 and 8, test head 23 includes preferably unitary test block 33 that has a pump 34, best illustrated in FIG. 6, a pressure relief valve 35, and a pressure release valve 36, both of which are shown schematically in top views in FIG. 5. A gauge 37, best shown in FIG. 1, is mounted on test block 33 and indicates the hydraulic pressure being applied to the ball as it contacts and indents the test piece.

Test block 33 has formed therein a ram cylinder 38 and a pump cylinder 41, both illustrated in FIG. 6, as well as a pressure relief valve chamber 42, shown in FIG. 7, and a pressure release valve chamber 43 shown in FIG. 8.

An oil sump 44, which is shown in FIG. 6 and may contain any suitable hydraulic fluid, is provided by a cuplike casing 45, which preferably is press-fitted into ram cylinder 38. The upper part of casing 45 has a flange 46 that makes oil-tight contact with the walls of ram cylinder 38.

As shown in FIG. 6, the upper end of ram cylinder 38 is threaded to receive a retaining nut 47, which bears against the upper surface of flange 46 to lock casing 45 in place. A flexible, hydraulic fluid-impenetrable sack 48 is positioned in oil sump 44. Sack 48 is preferably held in place by a threaded washer 51, which preferably engages threads on the inner wall of retaining nut 47. Sack 48 prevents oil from escaping from sump 44 and expands and contracts under varying oil conditions within sump 44. A cap 52 is threaded onto retaining nut 51, as illustrated in FIG. 6.

Casing 45 has only one exit port 53 leading away from sump 44, and has only one return port 54 leading back into sump 44. Ports 53 and 54 are illustrated in FIG. 5 and are spaced apart by about 95° in oil sump casing 45 in order to inhibit leakage therebetween.

As shown in FIG. 6, a cuplike ram 55 is positioned in ram cylinder 38 and has a ram pressure chamber 56 formed between the interior of ram 55 and the exterior of oil sump casing 45.

A low pressure valve 57, illustrated in FIG. 6, has a valve chamber 58 formed in block 33, and includes an entrance port 61 with a ball check valve 62 urged toward the closed position by one end of a preferable coil spring 63, which has its other end abutting a screw 64 threaded into the outside wall of block 33. Exit port 53, illustrated and numbered in FIG. 5, of sump 44 is connected to entrance port 61 of low pressure valve 57 by a passageway including duct 65 and vertical duct 66, both of which are illustrated and numbered in FIG. 6.

Low pressure valve chamber 58 is connected to pump cylinder 41 by a pump passageway including a vertical duct 67, as shown in FIG. 6.

Referring to FIG. 7, a high pressure valve 68 having a chamber 71 is also formed in block 33 and is provided with an entrance port 72. A ball check valve 73 resides in entrance port 72 and is urged towards the closed position by one end of a preferable coil spring 74 having its other end abutting a screw 75, which is threaded into the outside wall of block 33.

Still referring to FIG. 7, a passageway including duct 77 connects low pressure valve chamber 58 (shown and numbered in FIG. 6) to the entrance port 72 of high pressure valve 68, whereby oil may be pumped from pump cylinder 41 into the low pressure valve chamber 58 and then through duct 77 to the high pressure valve 68. The axis of the high pressure valve 68 is ninety degrees (90°) from the axis of low pressure valve 57. The passageway leading from high pressure valve chamber 71 to gauge 37 includes a duct 78, shown in FIG. 5, that is horizontally positioned, is ninety degrees (90°) from the axis of high pressure valve chamber 71, and is parallel to the axis of low pressure valve chamber 58. This makes for easy drilling of the valve chambers and ducts, since all except one are normal to the surface of the outside wall of test block 33 into which they are drilled when test block 33 is fabricated.

As illustrated in FIG. 7, high pressure valve chamber 71 is connected to pressure relief valve 35 (which is not illustrated in FIG. 7 to enhance drawing clarity but which is positioned in pressure relief valve chamber 42) through a passageway including a vertical duct 81. High pressure valve chamber 71 is also connected to pressure release valve 36 (which is not illustrated in FIG. 7 to enhance drawing clarity) by a passageway including horizontal duct 82. High pressure valve chamber 71 is yet further connected to gauge 37 through a passageway including a horizontal duct 78. Finally, high pressure valve chamber 72 is yet also connected to ram pressure chamber 56 through a passageway including a duct 83, illustrated and numbered in FIG. 5.

A return passageway including a diagonal duct 84, illustrated and numbered in FIG. 5, connects the pressure relief valve chamber 42 and the pressure release valve chamber 43 to oil sump 44 through return port 54.

Pump 34, which is shown generally in FIG. 6 (except for pump handle 91, which is illustrated in FIGS. 1 through 4), includes pump handle 91 attached to a shaft 92 to which is keyed a segmented gear 93, as shown in FIG. 6. Segmented gear 93 meshes with unnumbered rack teeth of a pump plunger 94 to move plunger 94 up and down thereby to pump oil from pump cylinder 41, through duct 67, and into low pressure valve chamber 58, all in response to manual reciprocating actuate movement of pump handle 91.

When pump plunger 94 is raised, oil is drawn from sump 44 through exit port 53 (shown in FIG. 5), through duct 65 and through vertical duct 66 (both shown in FIG. 6) into chamber 58, past ball check 62, and through duct 67 into pump cylinder 41, all as also shown in FIG. 6.

Then, as plunger 94 is moved downwardly by corresponding movement of pump handle 91, rotating shaft 92 and segmented gear 93, segmented gear 93 engages the rack teeth of pump plunger 94 and oil trapped within pump cylinder 41 is forced under pressure into valve chamber 58. Since ball check valve 62 is seated by the force of spring 63 and the pressure of the oil from pump cylinder 41, oil is forced under pressure through duct 77 shown in both FIGS. 6 and 7, to entrance port 72 of high pressure valve 68, both shown in FIG. 7, where the pressure of the oil forces the oil past ball check valve 73 into high pressure chamber 71.

Oil reaching high pressure chamber 71 cannot reverse its direction of flow due to the presence of ball 73, which seats due to the action of spring 74 when the pressure of the oil from duct 77 diminishes. As pumping continues, oil flows from high pressure chamber 71 through vertical duct 81 shown in FIG. 7, and horizontal duct 83 shown in FIG. 5, into ram pressure chamber 56 shown in FIG. 6. As more oil is forced into pressure chamber 56, pressure gradually builds therein to move hydraulic ram 55.

Ram pressure chamber 56 communicates with pressure gauge 37, pressure release valve 36, and pressure relief valve 35, so that oil pressure thereamong is uniform.

Pressure relief valve 35, described in more detail below, is manually preset to open at a selected oil pressure.

Figure 10:
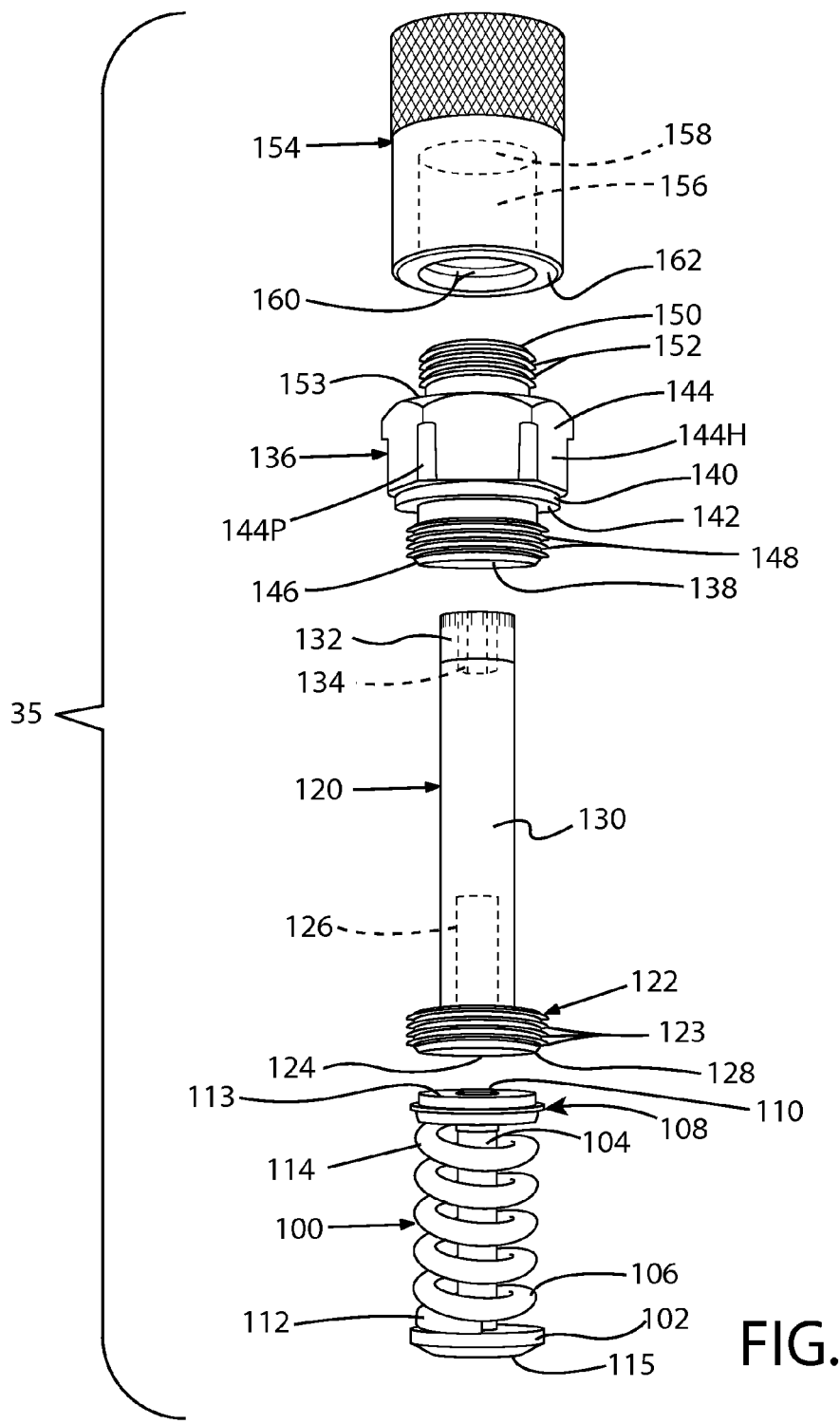
FIG. 10 is an exploded view of a adjustable pressure relief valve manifesting aspects of the invention, with views of some of the components taken looking slightly upwardly or downwardly, to provide depth to the drawing and thereby to enhance drawing clarity and ease of understanding.
Figure 11:
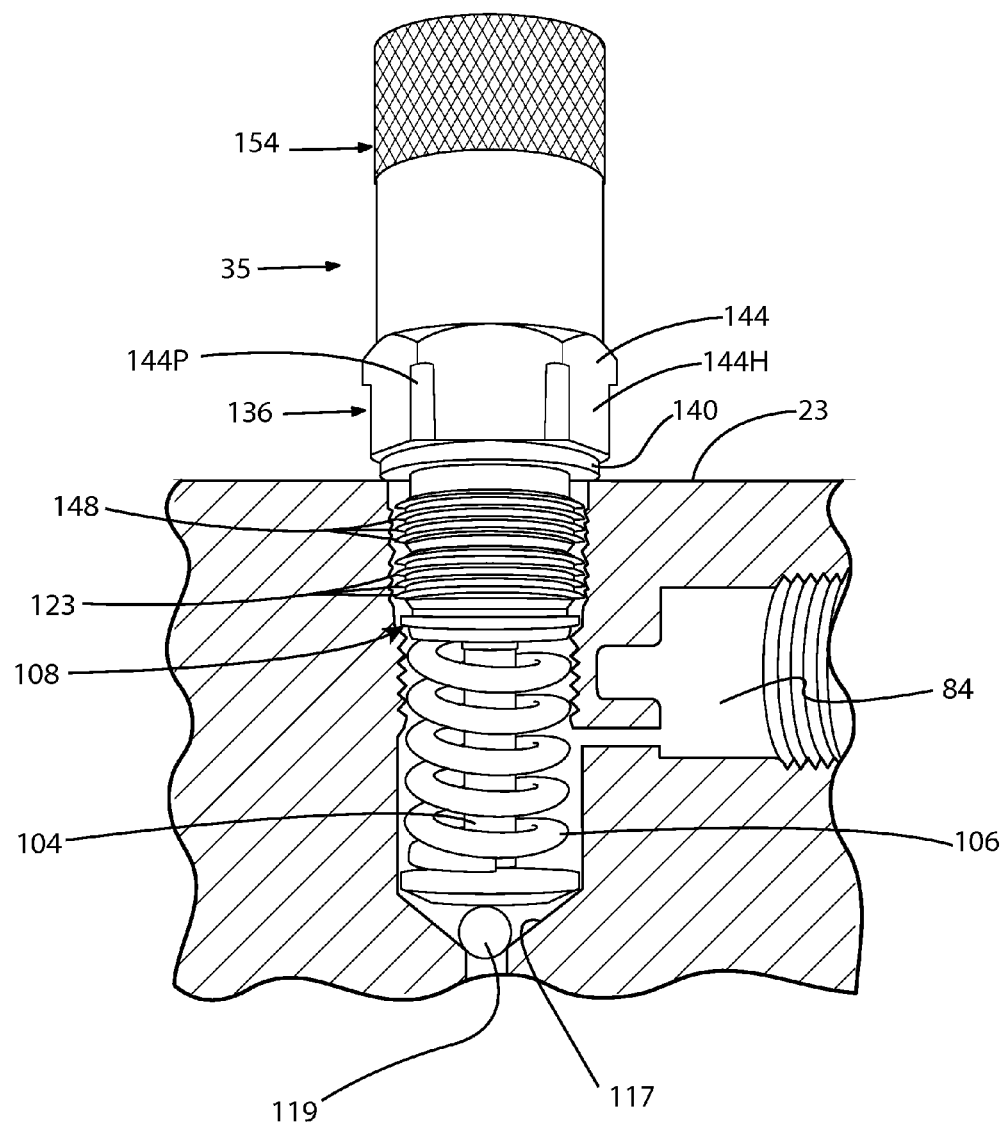
FIG. 11 is a sectional view taken at lines and arrows I-I in FIG. 5 of the adjustable pressure relief valve, shown in FIG. 10, assembled in place within the test head portion of the portable Brinell metal hardness tester illustrated in FIGS. 1 through 4 and 9, with views of some of the components taken looking slightly upwardly or downwardly, to provide depth to the drawing and thereby to enhance drawing clarity and ease of understanding.

Referring to the structure illustrated in FIGS. 10 and 11, when oil pressure is too high, oil pressure forces the circular head 102 of valve stem 100 of pressure relief valve 35 away from its seat and oil flows through the pressure relief valve chamber 42 depicted in FIG. 7, emptying into sump 44 through diagonal duct 84 and return port 54. Diagonal duct 84 is illustrated in FIGS. 5 and 11; return port 54 is illustrated in FIG. 5.

Pressure release valve 36 is manually operated by turning handle 300, which allows oil in high pressure duct 82 to flow through pressure release valve chamber 43 shown in FIG. 7, and through diagonal duct 84 to return to sump 44 via return port 54 as shown in FIG. 5.

Operation commences with pressure release valve 36 being opened by manually turning handle 300. Carriage 14 is raised enough to admit a test piece 31 into the space between anvil 24 and ball 28. Test piece 31 is then firmly clamped between ball 28 and anvil 24, making sure that ram 55 is pushed in (upwards in FIG. 6) as far as possible. Pressure release valve 36 is closed by manual movement of pressure release valve handle 300.

Pump handle 91 is then slowly manually reciprocated until the preselected full pressure, as shown on gauge 37, causes pressure relief valve 35 to "pop off" three or four times, assuring that the oil in ram pressure chamber 56 is at the preselected pressure at which pressure relief valve 35 has been set to relieve or "pop off". With high pressure oil in ram pressure chamber 56 pressing against ram 55, ram 55 urges ball 28 against test piece 31, creating the spherical indentation/impression that when measured in conjunction with the known hydraulic pressure yields the Brinell hardness of the test piece. Pressure release valve 36 is then manually opened, and carriage 14 is raised. The impression made by ball 28 on test piece 31 is a standard Brinell impression and it is read in the known manner.

As best illustrated in FIG. 2, base 11 is made with a narrow, shallow nose supporting anvil 24. This nose portion of base 11, extending beyond the front end of the bottom plate of base 11, allows tests to be made in small places, in tubes, and the like. This gives tester 10 unlimited possibilities for quickly making tests in places and on parts that otherwise would be too cumbersome or be impossible to test.

For applying lesser loads, i.e. loads less than the maximum setting of pressure relief valve 35, the procedure is to manually move pump handle 91 to increase hydraulic pressure to achieve the desired load, as indicated on the dial of gauge 37. The pressure is held for a few seconds, if necessary, and is then released. Such tests are accurate, even if the pressure relief valve 35 is not set to pop off automatically at these reduced loads.

For testing parts larger than those that will fit between anvil 24 and ball 28 when using base 11 and carriage 14, test head 23 may be removed from carriage 14 by removing screws 27. Parts of any size may then be tested by providing means, such as c-clamps and yokes, placed against cap 52 to take the thrust of the load.

Pressure relief valve 35 is illustrated in greater detail in FIGS. 10 and 11, being particularly well shown in exploded form in FIG. 10. Pressure relief valve 35 includes a valve stem designated generally 100, with valve stem 100 including a circular head 102 located at one end of valve stem 100. A shaft 104 is fixedly connected to and extends upwardly from circular head 102 into a central passageway 110 formed in cylindrical cap 108 of valve stem 100, with shaft 104 residing slidably in central passageway 110. A coil spring 106 is positioned between circular head 102 of valve stem 100 and cylindrical cap 108 of valve stem 100, with a first end of spring 106 riding on an annular planar surface 113 of circular head 102 of valve stem 100. The second end of spring 106 rests against a downwardly facing unnumbered annular surface of cylindrical cap 108, outboard of central passageway 110.

Circular head 102 of valve stem 100 further includes a downwardly facing (as respecting FIG. 10 and the position and orientation of pressure relief valve 35 depicted therein), generally rounded surface 115 configured for tight mating against a valve seat 117 formed in test head 23, as illustrated in FIG. 11. Optionally, a ball 119 may be provided, as illustrated in FIG. 11, for rounded surface 115 to bear against, thereby forcing ball 119 against an opening which would otherwise be at the vertex of valve seat 117, as illustrated in FIG. 11.

Pressure relief valve 35 is illustrated in greater detail in FIGS. 10 and 11, being particularly well shown in exploded form in FIG. 10. Pressure relief valve 35 includes a valve stem designated generally 100, with valve stem 100 including a circular head 102 located at one end of valve stem 100. A shaft 104 is fixedly connected to and extends upwardly from circular head 102 into a central passageway 110 formed in cylindrical cap 108 of valve stem 100, with shaft 104 residing slidably in central passageway 110. A coil spring 106 is positioned between circular head 102 of valve stem 100 and cylindrical cap 108 of valve stem 100, with a first end 112 of spring 106 riding on an annular planar surface 113 of circular head 102 of valve stem 100. The second end 114 of spring 106 rests against a downwardly facing unnumbered annular surface of cylindrical cap 108, outboard of central passageway 110.

Cylindrical end 122 of interior member 120 includes an annular surface 128 formed on first end 122 and facing oppositely from recess 124.

Interior member 120 further includes an elongated central cylindrical portion 130 and a cylindrical second end 132 in which a hexagonal receptacle 134, not visible in FIG. 10 and accordingly shown in dotted lines, is formed.

Still referring to FIG. 10, pressure relief valve 35 further includes an intermediate member designated generally 136, having an axial central passageway 138 extending therethrough, with the opening to passageway 138 being visible at the bottom end of passageway 138 in FIG. 10. Intermediate member 136 further includes an annular shoulder 140 formed on one surface of a generally hexagonally configured central portion 144 of intermediate member 136. Hexagonal central portion 144 has outwardly facing surfaces 144H, which give central portion its hexagonal configuration. Intermediate surfaces 144P are planar surfaces formed on central portion 144 of intermediate member 136, between the larger surfaces 144H that provide the generally hexagonal shape to hexagonal central portion 144 of intermediate member 136. A first end portion of intermediate member 136 is designated 146 and includes external threads formed thereon with the threads being designated 148. Intermediate member 136 further has a second end portion 150 on which are formed external threads 152.

Pressure relief valve 35 yet further preferably includes an external cap designated generally 154. Cap 154 includes an axial bore 156 formed therein. Axial bore 156 has a bottom 158 shown in dotted lines in FIG. 10. Internal threads 160 within bore 156 are of the same size and pitch as external threads 152 on second portion 150 of intermediate member 136. This allows threaded engagement of cap 154 with intermediate member 136 when pressure relief valve 135 is in position within test block 23, as illustrated in FIG. 11. Knurled surface 155 formed about the upper cylindrical outer surface of external cap 154 facilitates manual rotation and removal of cap 154 from pressure relief valve 35 when needed.

Referring to FIG. 10 and principally to FIG. 11 showing pressure relief valve 35 in position within test head 23, when pressure relief valve 35 is assembled, interior member 120, specifically the elongated central cylindrical portion 130 thereof, rides slidably within axial passageway 138 through intermediate member 136. Annular surface 128 formed on cylindrical end 122 of interior member 120 facingly contacts the outwardly facing extremity of first end portion 146 of intermediate member 136. External threads 123 on end 122 of interior member 120 are of the same size, pitch and diameter as external threads 148 on first end portion 146 of intermediate member 136, with threads 123, 148 being of the same size, facilitating threaded engagement with the internal threads 149 formed in the pressure relief valve chamber 42 in test head 23, as depicted in FIG. 11.

Still referring to FIGS. 10 and 11, recess 124 in first end 122 of interior member 120 is of cylindrical configuration and is sized to received cylindrical cap 108 of valve stem 100.

When pressure relief valve 35 is in the assembled condition illustrated in FIG. 11 and external cap 154 is removed therefrom, elongated central cylindrical portion 130 of interior member 120 extends slidably through the length of axial passageway 138 in intermediate member 136 and protrudes from second end portion 150 of intermediate member 136. This permits manual rotation of interior member 120 using a hexagonal wrench fitting into hexagonal receptacle 134 formed in cylindrical second end 132 of interior member 120, as illustrated in FIG. 10. As an operator manually rotates interior member 120 using a hexagonal wrench, interior member 120 moves vertically up or down within and respecting test head 23, according to the direction of rotation.

Considering a view from the top of FIGS. 10 and 11, clockwise rotation of interior member 120 results in interior member 120 moving downwardly. Since interior member 120 is in sliding contact with valve stem 100, with the contact occurring between recess 124 in first end 122 of interior member 120 and cylindrical cap 108 of valve stem 100, clockwise rotation and resulting downward movement of interior member 120 moves cylindrical cap 108 of valve stem 100 downwardly, thereby compressing spring 106 and increasing the closure force applied by circular head 102 either to ball 119 or against valve seat 117, depending on whether ball 119 is present or not. This increased closure force results in a higher required hydraulic pressure to open pressure relief valve 35 with the pressure resulting from oil being present in passageways 81 and 42, as shown in FIG. 7. When pressure relief valve 35 opens due to oil pressure exceeding a preselected level, oil escapes from pressure relief valve chamber 142 via passageway 84 depicted in FIG. 11 and also shown in FIG. 5.

Further in the assembled condition, and again considering the view from the top looking down in FIGS. 10 and 11, clockwise rotation of intermediate member 136 results in downward movement of intermediate member 136, due to engagement of external threads 148 on first end portion 146 of intermediate member 136 with the internal threads 149 in pressure relief valve chamber 42. Intermediate member 136 may be further rotated clockwise until the exteriorly facing annular surface 142 on annular shoulder 140 facingly contacts an upwardly facing planar exterior surface 90 of test head 23 in which internally threaded pressure relief valve chamber 42 is formed, as illustrated in FIG. 11.

Facing contact of axially facing annular surface 142 of external cap 154 with the exterior surface 90 of test head 23 provides a fluid-tight seal between pressure relief valve 35 and test head 23.

Once intermediate member 136 is in position with axially facing annular surface 142 of external cap 154 in facing tight contact with the exterior surface of test head 23, oil can only escape around or through pressure relief valve 35 to the exterior of test head 23 by travelling through passageway 138 formed in intermediate member 136, which passageway is occupied by elongated central cylindrical portion 130 of interior member 120. Since there is sliding contact between elongated central cylindrical portion 130 of interior member 120 and passageway 138 through intermediate member 136, a small amount of oil can seep between these two members. However, once threaded external cap 154 is screwed tightly into place on second end portion 150 of intermediate member 136, a fluid-tight seal is created and any oil seeping upwardly along the tiny clearance between the interior surface of passageway 138 through intermediate member 136 and central cylindrical portion 130 of interior member 120 is blocked by the resulting fluid-tight seal between the annular exterior surface 162 formed around bore 158 in external cap 154 and the upwardly facing annular surface 153 formed on second end portion 150 of intermediate member 136.

Figure 12:
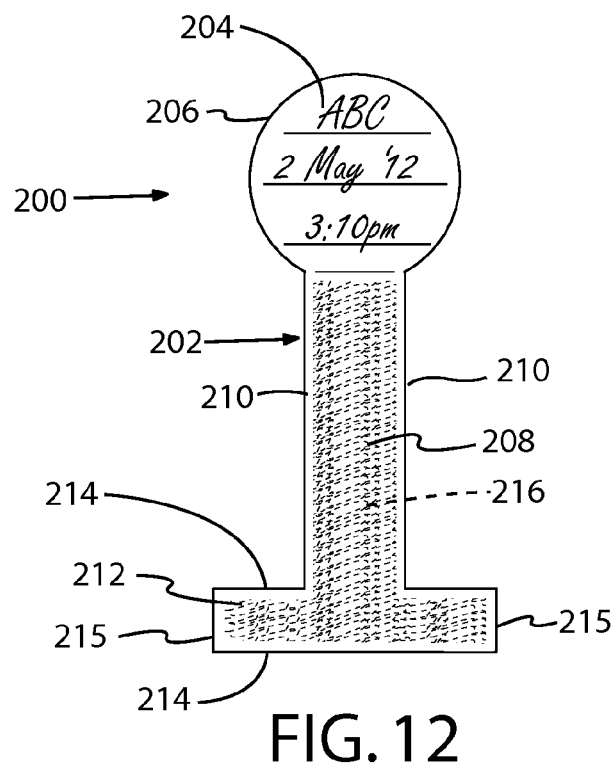
FIG. 12 is a plan view of one embodiment of a tamper indicator especially adapted for use with the pressure relief valve of the portable metal hardness tester illustrated in FIGS. 1 through 4 and 9.
Figure 13:
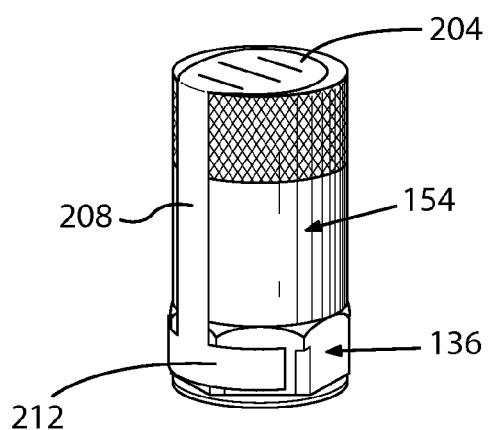
FIG. 13 is a isometric view of the external cap and an exposed part of the adjustable pressure relief valve illustrated in FIG. 10, in place in a test head of the portable metal hardness tester illustrated in FIGS. 1 through 10, showing the tamper indicator tape affixed thereto.

FIGS. 12 and 13 illustrate a tamper detector portion of the portable Brinell metal hardness tester of the invention, where the tamper detector is depicted generally as 200 and includes a sheet denoted 202. Sheet 202 includes a first portion 204 having a circular periphery 206. A second portion of sheet 202 is denoted 208 with parallel, spaced apart sides of second portion 208 both being denoted 210. Sheet 202 further includes a third portion 212, where the parallel, spaced apart sides of third portion 212 are both denoted 214 and the parallel, spaced apart ends of third portion 212 are both denoted 215.

Tamper detector 200 further includes adhesive 216, which has been denoted schematically in FIG. 12 as being on one side of sheet 202. In FIG. 12, adhesive 216 has been depicted as covering only a portion of FIG. 12, to enhance drawing clarity. However, it is to be understood that it is most desirable for adhesive 216 to cover one entire side of sheet 202 or even to be impregnated therein.

Sheet 202 may further include a crease 203 which may be a very narrow area, no wider than a pencil line, of reduced thickness or reduced strength, or both, thereby facilitating bending of first portion 204 relative to second portion 208 of sheet 202. Sheet 202 may also desirably include a second crease 205, also desirably no wider than a pencil line, of reduced thickness or reduced strength or both, facilitating separation of third portion 212 from second portion 208.

First portion 204 of sheet 202 desirably includes lines 205 on which a test operator may place identifying information such as the test operator's initials, the date that the tester was calibrated or the date the hydraulic fluid was changed, and the time of the calibration or change of hydraulic fluid. Lines for recording of such information thereon are indicated as 205 in FIG. 12, where exemplary information appears as would be written by an operator after either calibrating the tester or changing the hydraulic fluid, or both. Adhesive 216, or the adhesive side of sheet 202, is on the side of sheet 202 opposite from the side of sheet 202 an which lines 205 are located.

As further illustrated in FIG. 12, second portion 208 of sheet 202 has preferably parallel sides 210 and preferably extends radially away from first portion 204. Third portion 212 of sheet 202 connects to second portion 208, preferably at a position remote from juncture of first portion 204 and second portion 208 as defined by crease 203. Third portion 212 includes sides 214 that are preferably parallel one with another, and ends 215 that are also preferably parallel one with another and desirably positioned at right angles to sides 214.

Referring to FIG. 13, when sheet 202 is positioned on external cap 154 and intermediate member 136, adhesive 216 secures first portion 204 of sheet 202 to the circular outwardly facing top surface of external cap 154. Adhesive similarly secures second portion 208 of sheet 202 to the curved cylindrical side of external cap 154. Adhesive similarly secures third portion 212 of sheet 202 to one and preferably several of flat hexagonal panel surfaces 144H and to the flat surfaces 144P separating adjacent surfaces 144H of intermediate member 136, all as illustrated in FIG. 13. With this arrangement, once sheet 202 is in position and the adhesive has cured so that sheet 202 is bonded to external cap 154 and the intermediate member 136, a person cannot remove external cap 154 from threaded engagement with intermediate member 136 and the remainder of pressure relief valve 35 without fracturing sheet 202 at second crease 205 defining the juncture of second portion 208 and third portion 212. When an inspector sees a fracture of sheet 202 at crease 203 or proximate thereto, the inspector knows that someone has removed cap 154 and has likely tampered with pressure relief valve 35 of the metal hardness tester.

Sheet 202 may be paper or a polymer or any other suitable material. Sheet 202 preferably has one surface, opposite from the surface having adhesive 216 thereon, that accepts ink or other writing media so that the operator may place identifying information on sheet 202, as shown in FIG. 12.

Alternatively, adhesive 216 maybe supplied separately from sheet 202 and not coated on or impregnated therein. In such case, adhesive 216 is first applied to external cap 154 and intermediate member 136 of pressure relief valve 35 and then sheet 202 is marked with the appropriate time, date and operator identifying indicia, and then adhered to cap 165 and intermediate member 136 of pressure relief valve 35 using adhesive 216. Providing the operator identifying indicia, date and time are optional.

Desirably, the circular periphery of 206 of first potion 202 is of lesser diameter than external cap 154, as illustrated in FIG. 13, to facilitate placement and fitting of sheet 202 on and around external cap 154 and intermediate member 136.

Figure 3:
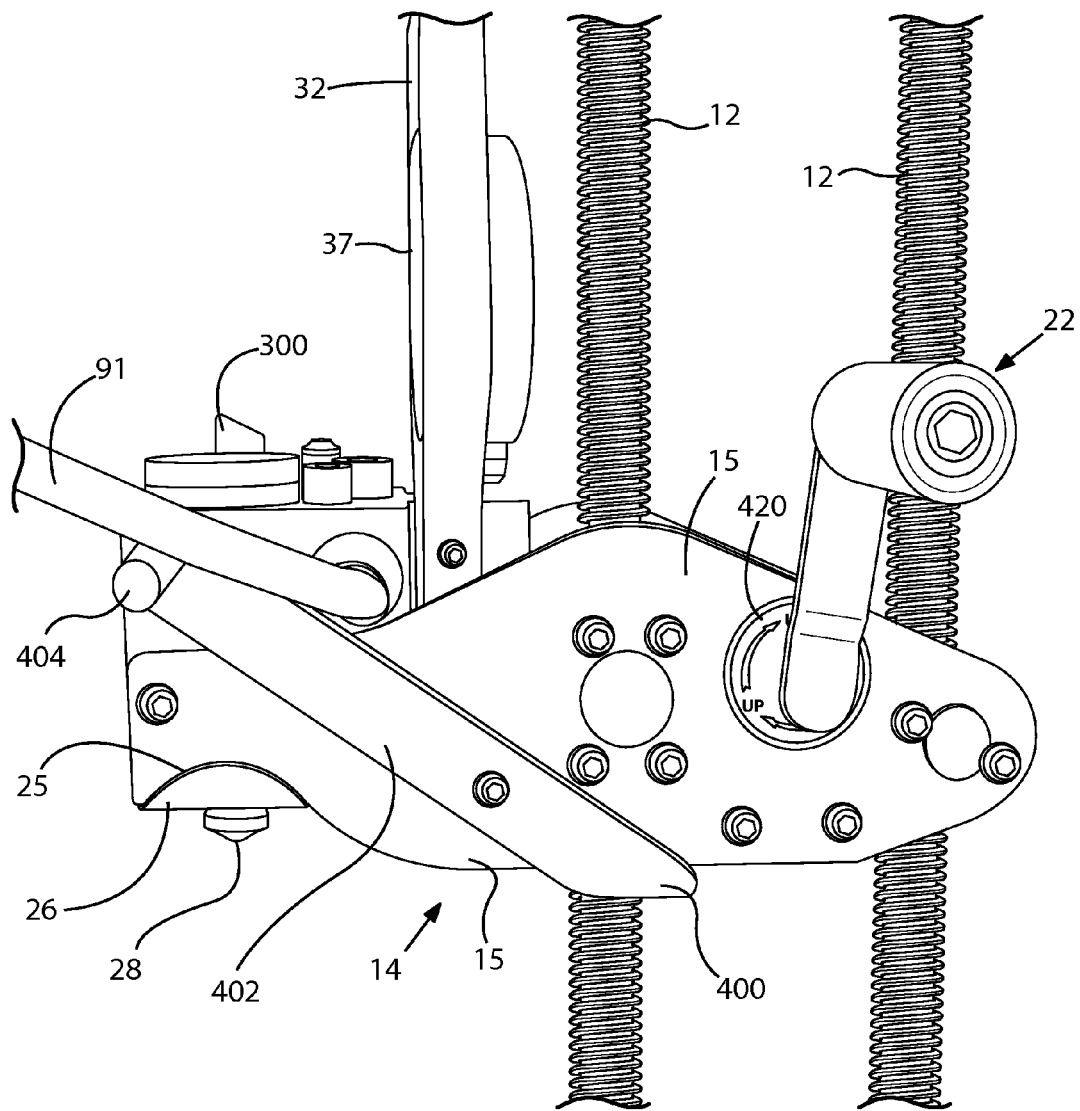
FIG. 3 is a broken side elevation, similar to FIG. 2, but with the pumping lever contacting the pump stroke limiter, with the view taken from slightly left of center to provide depth to the drawing, thereby to enhance drawing clarity and ease of understanding.
Figure 9:
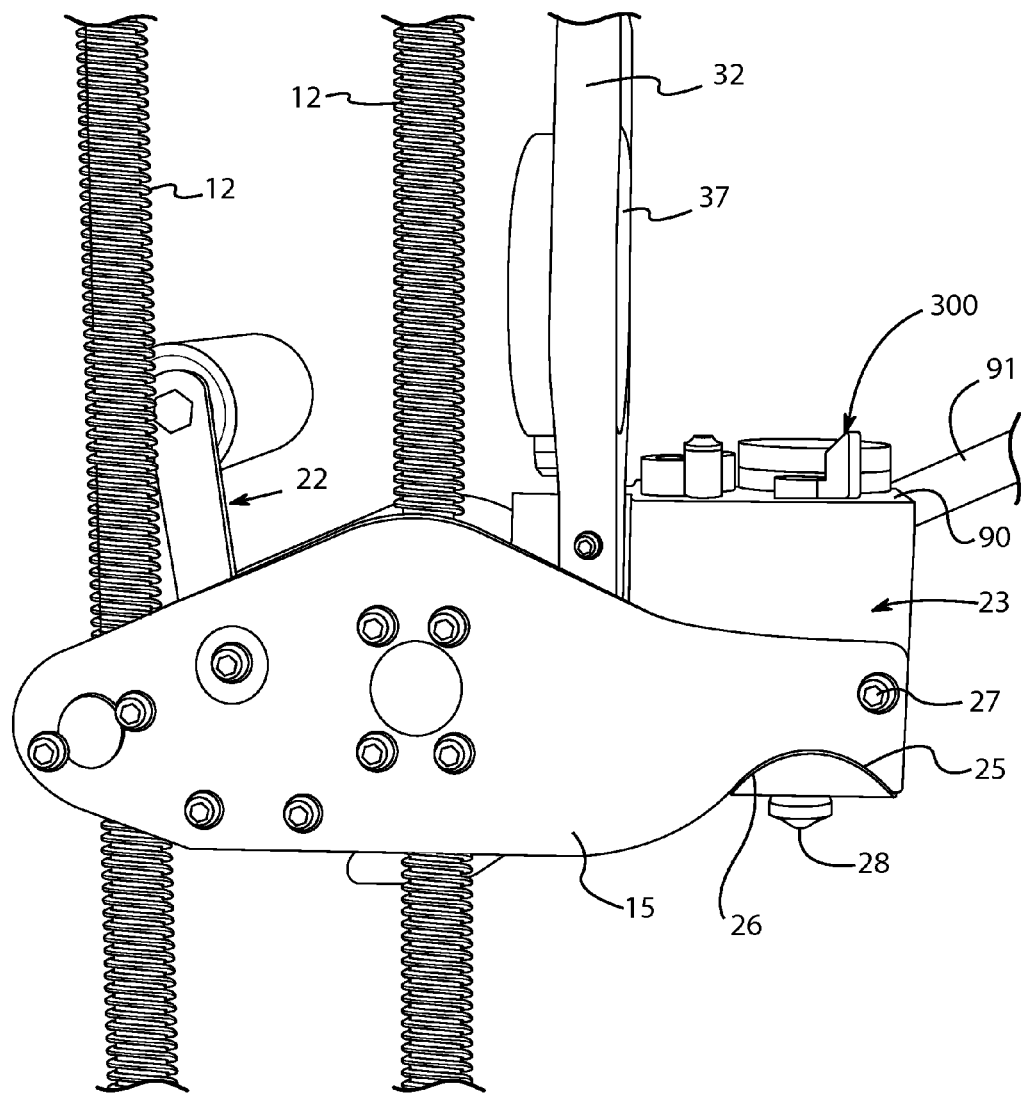
FIG. 9 is a broken right side elevation of the portable Brinell metal hardness tester illustrated in FIGS. 1 through 4, with the view taken from slightly right of center to provide depth to the drawing, thereby to enhance drawing clarity and ease of understanding.
Figure 14:
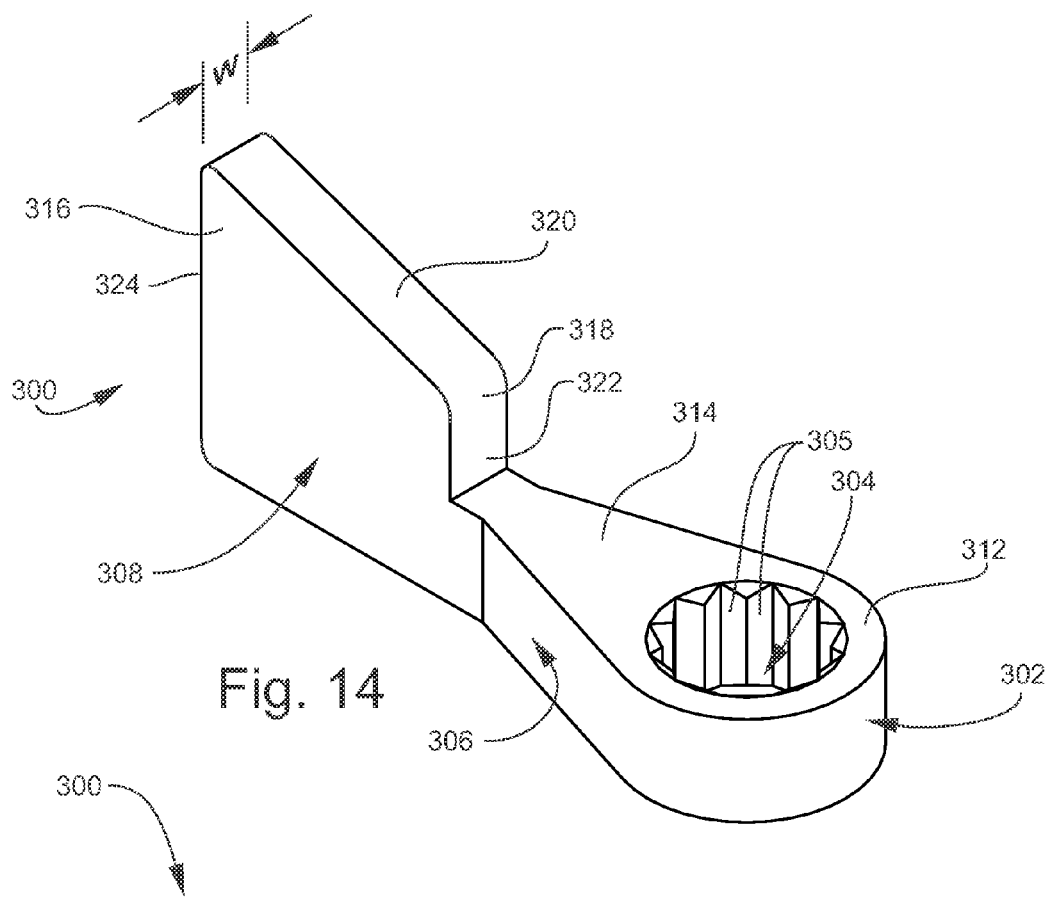
FIG. 14 is an isometric view of the top side, one side and one end of the handle for the pressure release valve handle of the portable metal hardness tester illustrated in FIGS. 1 through 9.
Figure 15:
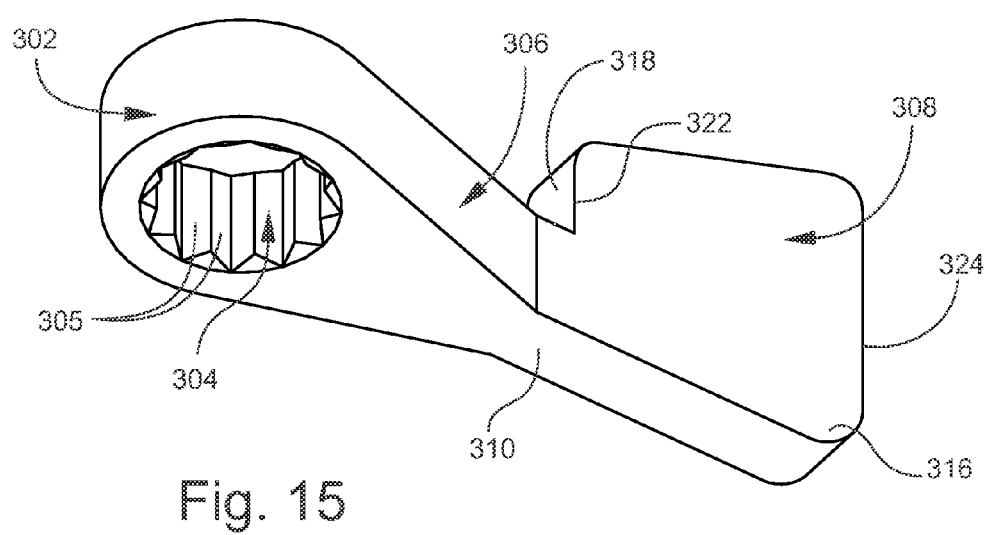
FIG. 15 is an isometric view of the bottom, the remaining side relative to that illustrated in FIG. 14, and the same end illustrated in FIG. 14 of the pressure release valve of the portable metal hardness tester illustrated in FIGS. 1 though 9.

FIGS. 14 and 15 are enlarged isometric views of pressure release valve handle 300 which is also visible in FIGS. 3, 4 and 9 of the drawings.

Referring to FIGS. 14 and 15, the pressure release valve handle is designated generally 300 and is used for releasing hydraulic fluid pressure when desired from the reservoir and passageways in test head 23 shown in FIGS. 1 through 9. Pressure release valve handle 300 preferably includes a ring-like portion 302 having an aperture 304 formed therein, with the aperture preferably being internally fluted, with the flutes being denoted 305 in FIGS. 14 and 15. Ring-like portion 302 with aperture 304 is sized for fitting over and receivingly gripping a rotatable shaft portion 303 of pressure release valve 36, which rotatable shaft portion extends externally of test head 23 at planar upper surface 90 thereof as illustrated in FIG. 4. Pressure release valve handle 300 preferably further includes an intermediate portion 306 connected to ring-like portion 302 and a blade portion 308 connected to intermediate portion 306, remotely from ring-like portion 302. Blade portion 308 is of generally upstanding planar configuration and is oriented in a co-planar relationship with an axis of shaft 303 of pressure release valve 36.

As best illustrated in FIG. 15, which is a view of the bottom surface of the pressure release valve handle 300, a lower or bottom surface of pressure release valve handle 300, designated 310, is preferably planar and extends and defines the entire lower surface of pressure release valve handle 300 when in place on the hardness tester. Planar lower surface 310 of pressure release valve handle 300 is flat for facing slidable contact with the upwardly facing planar exterior surface 90 of test head 23 as illustrated in FIG. 4 and in FIG. 9.

As shown in FIG. 14, ring-like portion 302 and intermediate portion 306 of pressure release valve 300 preferably have planar upper surfaces 312, 314, which are parallel with planar lower surface 310. Blade portion 308 has width designated by dimensional arrows and the letter "W" in FIG. 14 that is desirably less than the diameter of aperture 304. As best illustrated in FIG. 14, blade portion 308 preferably extends upwardly from planar lower surface 310 a greater distance than both intermediate portion 306 and ring-like portion 302. As further apparent from FIG. 14, intermediate portion 306 and ring-like portion 302 preferably extend upwardly from planar lower surface 310 a common distance.

As further evident from FIG. 14, a first part 316 of blade portion 308, which is remote from aperture 304, preferably extends upwardly from planar lower surface 310 a greater distance than a second part 318 of blade portion 308, which is more proximate to aperture 304. As further apparent from FIG. 14, a blade portion upper surface 320, which connects first and second parts 316, 318 of blade portion 308, is preferably a planar surface.

As further evident from FIG. 14 and from FIG. 15, blade portion 308 of pressure release valve handle 300 is of uniform transverse thickness. As still further evident from FIG. 14, the common distance that intermediate portion 306 and ring-like portion 302 extend upwardly from planar lower surface 310 is preferably greater than the transverse thickness of blade portion 308. As still additionally evident from FIG. 14, blade portion 308 has a first vertically extending edge 322 adjacent to intermediate portion 306 and a second vertically extending edge 324 positioned at an extremity of blade portion 308 that is remote from ring-like portion 302. As shown in FIG. 14, second vertically extending edge 324 is preferably longer than first vertically extending edge 322.

The configuration of pressure release valve handle 300 and particularly the configuration of blade portion 308, with second vertically extending edge 324 extending substantially upward a distance greater than the thickness of ring-like portion 302, facilitates easy gripping of pressure release valve handle 300 between an operator's thumb and index finger. This permits the operator to easily actuate pressure release valve 36 and, if desired, to open pressure release valve 36 thereby releasing hydraulic pressure within the tester.

In the preferred embodiment, the pressure release valve handle 300 has a thickness illustrated by dimensional arrows W in FIG. 14 of about one-eighth (⅛) of an inch. Blade portion 308 at its maximum height, denoted by dimensional arrow H in FIG. 15, is preferably about three-quarters (¾) of an inch. At the extremity of first vertically extending edge 322 of blade portion 308 remote from planar lower surface 310, the distance therefrom to planar lower surface 310 is preferably about one-half (½) of an inch. Height of the ring-like portion 302 and intermediate portion 306 measured from planar lower surface 310 is preferably about seven-sixteenths (⁷⁄₁₆) of an inch.

Pressure release valve handle 300 is preferably formed from a single piece of aluminum machined to the shape shown in FIGS. 14 and 15.

Referring to FIGS. 1, 2 and 3, and particularly to FIG. 3, the stroke limiter, providing another aspect of the invention, is adapted to be mounted on movable carriage 14 and includes a stop designated generally 400, which is connected to carriage 14 and positioned to contact the pump lever 91 at a predetermined limit of pump lever angular rotation, to thereby limit pump lever angular travel and thereby limit angular movement of the rotatable segmented gear 93, as illustrated in FIG. 6, to a predetermined amount. The stop is well shown in FIG. 3. Stop 400 includes a strap 402 which is preferably an elongated piece of steel secured to side plate 15 by at least one bolt, shown but not numbered in FIG. 3. Strap 402 is positioned in place by the unnumbered bolt that passes through strap 402 and by interference of strap 402 and particularly the upper edge thereof with an adjacent screw, as illustrated in FIG. 3. Once the bolt passing through strap 402 is secured in place, strap 402 is essentially immovable with respect to carriage 14.

A pump lever travel limiting member 404 extends perpendicularly from strap 402 at a position proximate one end of strap 402. Pump lever travel limiting member 404 interferes with pump lever 91 upon pump lever 91 exceeding a preselected amount of angular travel from the starting position, at which segmented gear 93 engages the uppermost teeth of the rack portion of pump plunger 94, as illustrated in FIG. 6. Lever travel limiting member 404 is preferably cylindrical in form and secured to strap 402, with the axis of the cylinder being perpendicular to strap 402 and with the lever travel limiting member being in the same geometric plane in which pump lever 91 travels. With this arrangement, when pump lever 91 is brought to the preselected desired limit of angular travel, pump lever 91 contacts and interferes with lever travel limiting member 404, whereby further rotation of pump lever 91 is precluded. Lever travel limiting member 404 may be machined as a part of strap 402 or may be secured thereto by suitable machine screws.

As further illustrated in FIG. 3, the portable Brinell hardness tester according to the invention is desirably equipped with elevator crank handle rotation indicators 420. These rotation indicators are desirably paper or polymer film, having adhesive on one side for attachment to side plate 15 of the carriage about the shaft that is rotated by hand crank assembly 22 to raise and lower carriage 14. The elevator crank handle rotation indicators 420 include arrows showing the correct direction of hand crank assembly 22 in order to raise carriage 14 relative to base 11 of the tester. As illustrated in FIG. 3, the elevator crank handle rotation indicators and the arrow-like indicia together with the word "up" show that crank assembly 22 must be turned in the clockwise direction, viewing FIG. 3, in order to raise carriage 14 along elevating screws 12.

Test head 23 has many advantages. The passageways for the low and high pressure valves are preferably bored from a solid block so that there is no seepage around valve seat inserts. Moreover, the difficult and tedious job of setting valve seats is eliminated.

The test head is easy to maintain. The essentially integral construction of test head 23 permits the use of heavy ball-check springs. Accordingly, pressure builds quickly, and there is little back flow of oil through the ball check valves. The strong springs enable the tester to hold the pressure once pressure has built up.

Test head 23 is easy to construct because there are few ducts and holes, there are no inserts except for springs and valves, and tolerances need not be maintained particularly high. In test head 23, there are only two holes or ports between sump 44 and the wall of ram cylinder 38 and they are placed about 95° apart so that there is little chance of seepage.

In the preferred embodiment, test head 23 weighs only about ten pounds so it is quite portable.

The following is claimed:

1. A portable Brinell metal hardness tester having a test head mounted in a carriage and movable vertically along elevating screws, for applying preselected force to a test piece by pumping of hydraulic fluid by manual movement of a pumping lever to apply hydraulic fluid pressure of a prescribed level to a ball contacting a test piece, comprising:
(a) an adjustable valve for relieving hydraulic fluid pressure within the test head upon reaching an adjustably selected level, comprising:
(i) a stem comprising:
(1) a head for fitting against a seat;
(2) a shaft connected to the head;
(3) a spring abutting the head and residing slidably about the shaft;
(4) a cap having a passageway therethrough for slidable passage of the shaft therewithin;
(5) the spring contacting the cap remotely from the head and resiliently compressingly resisting movement of the head away from the seat;
ii) an interior member comprising:
(1) a first end receiving the cap and being externally threaded for engagement with a threaded passageway;
(2) a second end for receiving a wrench, for manual rotation of the interior member;
iii) an intermediate member having a central passageway extending axially therethrough and comprising:
(1) a central portion having an axially facing annular surface;
(2) a first end portion extending coaxially with the central passageway;
iv) a second end portion, extending coaxially with the central passageway, and being externally threaded at the end thereof remote from the central portion;
the interior member first end receiving the cap of the stem, with the bore in the interior member being positioned to receive the shaft upon axial movement of the head and resultant compression of the spring;
a central portion of the interior member extending slidably through the central passageway of the intermediate member;
rotation of the interior member within the threaded passageway moving the cap axially, with the valve stem exerting greater or lesser force at the valve seat according to the direction of axial movement of the interior member compressing or relieving the spring;
(b) a handle for a manually actuable valve for releasing hydraulic pressure within the test head, the handle comprising:
(i) a ring-like portion with an internally fluted aperture formed therein for fitting over and receivingly gripping a shaft portion of the pressure release valve;
(ii) an intermediate portion connected to the ring-like portion;

(iii) a blade portion connected to the intermediate portion remote from the ring-like portion, being of generally upstanding planar configuration and oriented in a co-planar relationship with an axis about which the shaft rotates;
(c) a valve tampering detector, comprising:
  (i) a laminar sheet, comprising:
    (1) a first portion having a circular periphery for fitting on the circular top of a cylindrical external cap of the valve;
    (2) a second portion having parallel sides and extending radially away from the first portion; and
    (3) a third portion connected to the second portion remotely from the first portion, having parallel sides that are perpendicular to the sides of the second portion;
  ii) adhesive on the sheet for securing the sheet first portion to the cylindrical cap and the sheet third portion to a valve intermediate portion extending from the test head so that the sheet must be torn when separating the cap from the valve intermediate portion; and
(d) a stroke limiter for limiting movement of the pumping lever, comprising:
  (i) the pumping lever being mounted on a rotatable shaft connected to the test head;
  (ii) gear means within the test head for converting rotary motion of the lever into longitudinal movement of a hydraulic fluid pumping piston within the test head; and
  (iii) a stop connected to the a carriage portion of the tester for limiting angular movement of the lever with the shaft.

2. A pressure relief valve adapted to reside within a threaded passageway extending into a hydraulic fluid pressure chamber from an exterior surface thereof, for releasing hydraulic fluid therefrom upon pressure of the hydraulic fluid exceeding a preselected manually adjustable level required to open the valve, comprising:
(a) a valve stem comprising:
  i) a circular head for fitting fluid sealingly against a seat formed in the passageway at the fluid pressure chamber;
  ii) a shaft having a first end fixedly connected to the head and extending coaxially therefrom;
  iii) a coil spring having a first end abutting the head, the spring residing slidably about the shaft;
  iv) a cylindrically configured cap having a central passageway therethrough for slidable passage of the shaft, the cap having a first portion of greater diameter and an adjoining second portion of lesser diameter;
  v) a second end of the spring contacting the cap portion of greater diameter annularly outboard of the central passageway, the spring resiliently compressingly resisting movement of the head away from the seat and resultant sliding movement of the shaft within the passageway through the cap;
(b) an axially elongated interior member comprising:
  (i) a cylindrical first end having a recess for receiving the second portion of the cap therewithin, an axial bore opening into the recess, the first cylindrical end being externally threaded for engagement with the threaded passageway and having an annular surface facing axially oppositely from the opening to the recess;
  (ii) an elongated central cylindrical portion of lesser diameter than the first end, the axial bore extending into the elongated central cylindrical portion; and
  (iii) a cylindrical second end having common diameter with the central portion with an axially facing hexagonal receptacle for receiving a wrench, for manual rotation of the interior member;
(c) an axially elongated intermediate member having a central cylindrical passageway extending therethrough and comprising:
  i) a central portion having a hexagonal exterior, an annular shoulder being formed about the passageway on one end of the central portion and having an axially facing annular surface formed on the opposite end of the central portion;
  ii) a larger first end portion of generally tubular configuration extending coaxially with the central cylindrical passageway, being externally threaded for mating engagement with the threaded passageway, and having an axially facing annular surface at the axial extremity thereof remote from the central portion;
  iii) a smaller second end portion of generally tubular configuration, extending coaxially with the central cylindrical passageway, and being externally threaded at the end thereof remote from the central portion;
(d) a generally cylindrical external cap having a cylindrical axial bore, the bottom of the bore being closed, the bore being threaded for engagement with the smaller second end portion of the intermediate member, with an annular surface formed about the opening to the bore;
the recess of the interior member cylindrical first end fitting over and receiving the lesser diameter second portion of the cylindrically configured cap of the stem with the bore in the interior member cylindrical first end positioned to receive the shaft upon axial movement of the head and resultant compression of the spring;
the external threads on the interior member first end being of the same diameter and pitch as those on the externally threaded surface of the larger first end of the intermediate member;
both sets of external threads threadedly engaging the threaded passageway;
an axially facing annular surface of the cylindrical first end of the interior member and an axially outwardly facing annular surface of the intermediate member first end being in facing contact;
the elongated central cylindrical portion of the interior member extending slidably through the central cylindrical passageway of the intermediate member and into the cylindrical bore of the external cap;
the threaded cylindrical bore of the external cap engaging complemental external threads on the second end portion of the intermediate member;
the annular surface of the central portion of the intermediate member and the annular surface of the external cap being in facing contact;
whereby, when the external cap is removed, the cylindrical second end of the interior member extends slidably through and outwardly of the intermediate member, providing access to the hexagonal receptacle of the interior member first end such that upon wrench rotation of the interior member, due to the threaded engagement thereof with the threaded passageway the interior member moves axially within the threaded passageway and moves the cap axially, with the valve stem exerting greater or lesser force at the valve seat according to the direction of axial movement of the interior member compressing or relieving the spring.

3. A adjustable pressure relief valve comprising:
(a) a stem comprising:
 (i) a head for fitting against a seat;
 (ii) a shaft connected to the head;
 (iii) a spring abutting the head and residing slidably about the shaft;
 (iv) a cap having a passageway for slidable passage of the shaft therethrough;
 (v) the spring contacting the cap remotely from the head and resiliently compressingly resisting movement of the head away from the seat;
(b) an interior member comprising:
 i) a first end receiving the cap and being externally threaded for engagement with a threaded passageway;
 ii) a central portion;
 iii) a second end for receiving a wrench, for manual rotation of the interior member;
(c) an intermediate member having a central passageway extending therethrough and comprising:
 i) a central portion having an axially facing annular surface;
 ii) a first end portion extending coaxially with the central passageway;
 iii) a smaller second end portion of generally tubular configuration, extending coaxially with the central passageway, and being externally threaded at the end thereof remote from the central portion;
(d) a removable external cap having a threaded internal bore for threaded engagement with the second end portion of the intermediate member;
the interior member first end receiving the cap of the stem, with the bore in the interior member positioned to receive the shaft upon axial movement of the head and resultant compression of the spring;
the central portion of the interior member extending slidably through the central passageway of the intermediate member and into the bore of the external cap;
the threaded bore of the external cap engaging complemental threads on the second end portion of the intermediate member;
the intermediate member and the external cap being in facing contact;
such that upon rotation of the interior member, due to the threaded engagement thereof with the threaded passageway, the interior member moves within the threaded passageway and moves the cap axially, with the valve stem exerting greater or lesser force at the valve seat according to the direction of axial movement of the interior member compressing or relieving the spring.

4. The valve of claim 3 wherein an axially facing surface of the first end of the interior member and an axially facing surface of the intermediate member first end are in facing contact.

5. The valve of claim 3 wherein the threaded bore of the external cap engages complemental threads on the second end portion of the intermediate member.

6. The valve of claim 3 wherein the second end of the interior member extends slidably through and outwardly of the intermediate member, so as to provide, in the absence of the external cap, access to the interior member first end.

7. A adjustable pressure relief valve comprising:
(a) a stem comprising:
 i) a head for fitting against a seat;
 ii) a shaft connected to the head;
 iii) a spring abutting the head and residing slidably about the shaft;
 iv) a cap having a passageway therethrough for slidable passage of the shaft therewithin;
 v) the spring contacting the cap remotely from the head and resiliently compressingly resisting movement of the head away from the seat;
(b) an interior member comprising:
 (i) a first end receiving the cap and being externally threaded for engagement with a threaded passageway;
 ii) a second end for receiving a wrench, for manual rotation of the interior member;
(c) an intermediate member having a central passageway extending axially therethrough and comprising:
 i) a central portion having an axially facing annular surface;
 ii) a first end portion extending coaxially with the central passageway;
(d) a second end portion, extending coaxially with the central passageway, and being externally threaded at the end thereof remote from the central portion;
the interior member first end receiving the cap of the stem, with the bore in the interior member being positioned to receive the shaft upon axial movement of the head and resultant compression of the spring;
a central portion of the interior member extending slidably through the central passageway of the intermediate member;
rotation of the interior member within the threaded passageway moving the cap axially, with the valve stem exerting greater or lesser force at the valve seat according to the direction of axial movement of the interior member compressing or relieving the spring.

8. A portable Brinell metal hardness tester having a test head for applying preselected force to a test piece by manual pumping of hydraulic fluid to apply hydraulic fluid pressure of a prescribed level to a ball contacting a test piece, the test head including an adjustable valve for relieving hydraulic fluid pressure upon reaching an adjustably selected level, the adjustable valve comprising:
(a) a stem comprising:
 i) a head for fitting against a seat;
 ii) a shaft connected to the head;
 iii) a spring abutting the head and residing slidably about the shaft;
 iv) a cap having a passageway therethrough for slidable passage of the shaft therewithin;
 v) the spring contacting the cap remotely from the head and resiliently compressingly resisting movement of the head away from the seat;
(b) an interior member comprising:
 i) a first end receiving the cap and being externally threaded for engagement with a threaded passageway;
 ii) a second end for receiving a wrench, for manual rotation of the interior member;
(c) an intermediate member having a central passageway extending axially therethrough and comprising:
 i) a central portion having an axially facing annular surface;
 ii) a first end extending coaxially with the central passageway;
(d) a second end, extending coaxially with the central passageway, and being externally threaded at the end thereof remote from the central portion;
the interior member first end receiving the cap of the stem, with the bore in the interior member being positioned to receive the shaft upon axial movement of the head and resultant compression of the spring;

a central portion of the interior member extending slidably through the central passageway of the intermediate member;

rotation of the interior member within the threaded passageway moving the cap axially, with the valve stem exerting greater or lesser force at the valve seat according to the direction of axial movement of the interior member compressing or relieving the spring.

9. A portable Brinell metal hardness tester having a test head for applying preselected force to a test piece by manual pumping of hydraulic fluid to apply hydraulic fluid pressure of a prescribed level to a ball contacting a test piece, the test head including an adjustable valve for relieving hydraulic fluid pressure upon reaching an adjustably selected level, the adjustable valve comprising:

(a) a stem comprising:
   i) a head for fitting against a seat;
   ii) a shaft connected to the head;
   iii) a spring abutting the head and residing slidably about the shaft;
   iv) a cap having a passageway for slidable passage of the shaft therethrough;
   v) the spring contacting the cap remotely from the head and resiliently compressingly resisting movement of the head away from the seat;

(b) an interior member comprising:
   i) a first end receiving the cap and being externally threaded for engagement with a threaded passageway;
   ii) a central portion;
   iii) a second end for receiving a wrench, for manual rotation of the interior member;

(c) an intermediate member having a central passageway extending therethrough and comprising:
   i) a central portion having an axially facing annular surface;
   ii) a first end portion extending coaxially with the central passageway;
   iii) a smaller second end portion of generally tubular configuration, extending coaxially with the central passageway, and being externally threaded at the end thereof remote from the central portion;

(d) a removable external cap having a threaded internal bore for threaded engagement with the second end portion of the intermediate member;

the interior member first end receiving the cap of the stem, with the bore in the interior member positioned to receive the shaft upon axial movement of the head and resultant compression of the spring;

the central portion of the interior member extending slidably through the central passageway of the intermediate member and into the bore of the external cap;

the threaded bore of the external cap engaging complemental threads on the second end portion of the intermediate member;

the intermediate member and the external cap being in facing contact;

such that upon rotation of the interior member, due to the threaded engagement thereof with the threaded passageway, the interior member moves within the threaded passageway and moves the cap axially, with the valve stem exerting greater or lesser force at the valve seat according to the direction of axial movement of the interior member compressing or relieving the spring.

10. The tester of claim 9 wherein an axially facing surface of the first end of the interior member and an axially facing surface of the intermediate member first end are in facing contact.

11. The tester of claim 9 wherein the threaded bore of the external cap engages complemental threads on the second end portion of the intermediate member.

12. The tester of claim 9 wherein the second end of the interior member extends slidably through and outwardly of the intermediate member, so as to provide, in the absence of the external cap, access to the interior member first end.

* * * * *